US009750900B2

(12) United States Patent
Brunnberg et al.

(10) Patent No.: US 9,750,900 B2
(45) Date of Patent: Sep. 5, 2017

(54) METERED LIQUID DROPLET INHALER

(75) Inventors: Lennart Brunnberg, Tyresö (SE); Martin Karlsson, Göteborg (SE); Nils Ronquist, Stockholm (SE)

(73) Assignee: SHL Group AB, Nacka Strand (SE)

( * ) Notice: Subject to any disclaimer, the term of this patent is extended or adjusted under 35 U.S.C. 154(b) by 1115 days.

(21) Appl. No.: 13/500,915

(22) PCT Filed: Sep. 13, 2010

(86) PCT No.: PCT/SE2010/050972
§ 371 (c)(1),
(2), (4) Date: May 13, 2012

(87) PCT Pub. No.: WO2011/043712
PCT Pub. Date: Apr. 14, 2011

(65) Prior Publication Data
US 2012/0216805 A1 Aug. 30, 2012

(30) Foreign Application Priority Data
Oct. 8, 2009 (SE) ...................................... 0950738

(51) Int. Cl.
*A61M 5/00* (2006.01)
*A61M 11/06* (2006.01)
(Continued)

(52) U.S. Cl.
CPC ...... *A61M 15/0065* (2013.01); *A61M 11/007* (2014.02); *A61M 11/06* (2013.01);
(Continued)

(58) Field of Classification Search
CPC .. A61M 11/16; A61M 15/00; A61M 15/0065; A61M 15/0066; A61M 15/0096;
(Continued)

(56) References Cited

U.S. PATENT DOCUMENTS 6,221,046 B1 * 4/2001 Burroughs ........ A61M 5/31551 604/153
7,131,439 B2 * 11/2006 Blacker et al. .......... 128/200.18
(Continued)

FOREIGN PATENT DOCUMENTS

EP 1020233 A1 7/2000
WO 01/08732 A1 2/2001

OTHER PUBLICATIONS

Swedish Patent Office, Int'l Search Report in PCT/SE2010/050972, Jan. 20, 2011.

*Primary Examiner* — Todd J Scherbel
*Assistant Examiner* — Elliot S Ruddie
(74) *Attorney, Agent, or Firm* — Piedmont Intellectual Property

(57) ABSTRACT

A metered liquid droplet inhaling device includes a chassis; a holder releasably connected to the chassis; a container in the holder having a chamber for a composition, an opening for expelling the composition, and a piston; a dose knob accessible outside the chassis for setting a dose to be expelled by accumulating a rotational force; a power supply mechanism for converting the rotational force into an axial force applied to the piston; an activation device connected to the power supply mechanism; a mouth piece connected to the container holder and having a mouth engaging area and an air opening; a droplet generator arranged in the mouth piece and having a plurality of through passing orifices in fluid communication with the opening of the container and with the mouth piece; and a rotation damping member connected to the power supply mechanism for damping an initial pressure peak inside the container.

20 Claims, 17 Drawing Sheets

(51) Int. Cl.

*A61M 11/00* (2006.01)
*A61M 5/315* (2006.01)
*A61M 5/20* (2006.01)
*A61M 15/00* (2006.01)

(52) U.S. Cl.

CPC .... *A61M 15/0021* (2014.02); *A61M 15/0066* (2014.02); *A61M 15/0095* (2014.02); *A61M 15/0096* (2014.02); *A61M 5/2033* (2013.01); *A61M 5/31525* (2013.01); *A61M 5/31553* (2013.01); *A61M 5/31583* (2013.01)

(58) Field of Classification Search

CPC A61M 11/007; A61M 15/0021; A61M 11/06; A61M 5/31553; A61M 5/31583; A61M 15/025; A61M 11/006; A61M 11/08

USPC ............. 128/200.11–200.24, 203.12, 203.15, 128/205.24; 239/329, 331, 332, 333; 222/282, 287, 308, 309, 386; 604/186, 604/207, 246, 251, 407

See application file for complete search history.

(56) References Cited

U.S. PATENT DOCUMENTS

| | | | | |
|---|---|---|---|---|
| 2002/0161344 | A1 | 10/2002 | Peclat et al. | |
| 2003/0005926 | A1* | 1/2003 | Jones et al. | 128/200.23 |
| 2006/0276753 | A1* | 12/2006 | Kronestedt et al. | 604/186 |
| 2007/0256688 | A1* | 11/2007 | Schuster et al. | 128/200.23 |
| 2009/0234297 | A1* | 9/2009 | Jennings | A61M 5/2033 604/195 |
| 2011/0271958 | A1* | 11/2011 | Sawant | 128/203.21 |

* cited by examiner

METERED LIQUID DROPLET INHALER

TECHNICAL AREA

The present invention relates a metered liquid droplet inhaler.

BACKGROUND OF INVENTION

There are a large number of devices for delivering medication orally for absorption in the respiratory system and one strong trend is to develop inhalation devices for self-administration. Traditionally oral medication was intended for treatment of diseases in the trachea, bronchi and/or lungs, and in particular Acute or chronic symptoms of asthma. However, much research is now performed on administration of medicament via the lungs of other ailments due to beneficial absorption rate and reduced side effects. Further, pulmonary administration provides a greater safety than delivery devices using needles because of the problem with possible contamination from a used needle.

However, there are a number of medicament compositions that are not compatible with existing devices and there are further a number of drawbacks with existing devices. For example aerosol dispensers utilise a propellant which provides the force to aerosolize the medicament in liquid form. However, this requires a special type of pressurised canister containing liquid propellant which affects the environment. Also the ballistic aerosol has a very high speed which gives a large mouth and throat deposition giving more side effects.

Many of the devices on the market are also not very precise or reliable regarding repeated, equal dose quantities delivered. Another difficulty with some devices and/or medicament compositions is requirements regarding droplet size, drooling and also coordination between inhalation and dose delivery.

One example of a device which could be used for metered oral administration is described in the document WO 06/130100. The disclosed device comprises a plunger rod, which, when driven by a pre-tensioned helical spring, forces a stopper into a cartridge containing medicament, whereby a dose of medicament is delivered from an administration member. The administration member could be a mouth or nasal piece. While the device offers a reliable and precise dosing mechanism, there is no teaching regarding how to configure the medicament administrating member or how adjustments could be made for a variety of medicaments having different physical properties.

There are also numerous devices for delivering medicament on the market and also patented where the medicament is arranged in a generally tubular compartment having a stopper in one end of the compartment and a delivery member attached to the opposite end of the compartment, such as e.g. a needle, a medicament droplet generator or the like member capable of delivering medicament to a patient.

In order to deliver a quantity of medicament, the stopper is exposed to pressure, i.e. pushed into the compartment by a plunger rod, which could be done manually by a finger, which is the case for simple handheld syringes, or by pressure means such as springs, which is common in automatic or semi-automatic injectors.

In many instances it is desirable to be able to deliver a certain specified quantity of the medicament. This is for example the case with a multi-dose injection device, which is capable of delivering a number of specified, set, doses until the compartment is empty. One example is disclosed in the European patent application No. 05104734.8 where specific doses can be set before injection. The injection device disclosed is arranged with spring means for exerting a pressure on the medicament for delivering a specific dose, i.e. pushing the plunger rod and thus the stopper into the container.

The delivery of a dose requires a certain force from the spring means in order to overcome the friction between the somewhat resilient stopper and the inner surface of the cartridge and also to be able to press the medicament in liquid form through a rather small passage in the delivery member, possibly within a predetermined time.

Due to the elasticity of the components under pressure such as the stopper, air or gas, and also the medicament if non-newtonian, there is a prevailing pressure even when the stopper has been moved a predetermined distance and the dose has been delivered. This is in particular pronounced when handling medicament with rather high viscosity, medicament having resilient properties, and with high working pressures.

With this type of substance with high viscosity, and because very small passages of the delivery member often are used, a rather large force is required and because of the elasticity of the components, often a certain small quantity of the substance comes out of the delivery member even after performed delivery when the pressure is relieved, i.e. there is some drooling from the delivery member causing a waste of medicament and thereby decreasing the dose accuracy.

One solution is disclosed in WO 2008/020023 A1. Here a device is described for repeated dosing of small quantities of medicament. The device is particularly suitable for viscous liquids because it comprises a feature which releases pressure on the medicament inside the medicament container after delivery of a dose. This reduces the risk of dripping or drooling from the device after dose delivery.

There is thus still a need for accurate devices which facilitate oral administration of medicaments in liquid form for respiratory absorption which can be used with a variety of medicament compositions, where preferably the primary package, i.e. the medicament container, constitutes a standard and/or standard size container or syringe.

BRIEF DESCRIPTION OF INVENTION

The aim of the present is to remedy the drawbacks of the state of the art devices. This aim is obtained by the present invention comprising the features of the independent patent claims. Preferable embodiments of the present invention form the subject of the dependent patent claims.

According to a main aspect of the invention it is characterised by a metered liquid droplet inhaling device for delivering medicament, comprising a generally elongated tubular chassis having opposite distal and proximal ends; a medicament container holder releasably connected to said chassis by first engagement means; a medicament container arranged inside said medicament container holder, wherein said container comprises a tubular form having at least one chamber capable of containing a composition, a proximal opening for allowing the composition to be expelled therefrom, and at least one axially movable piston; a dose knob accessible outside the distal end of the chassis for setting a dose to be expelled by accumulating a rotational force; a power supply mechanism capable of converting the rotational force into an axial force to be applied to the piston and thereby create a pressure inside said medicament container; activation means in mechanical connection to the power supply mechanism; a mouth piece in mechanical connection to the proximal part of the container holder, where the mouth piece comprises a mouth engaging area and an air opening; a droplet generator having a plurality of through passing orifices and arranged in the mouth piece, wherein the orifices are in fluid communication with the proximal opening of the container and with the mouth piece; wherein the device further comprises a rotation damping member in mechanical connection to the power supply mechanism for damping an initial pressure peak inside said medicament container.

According to another aspect of the invention, the power supply mechanism comprises a threaded plunger rod having opposite distal and proximal ends, and having its proximal end in contact with the piston of the medicament container; a drive nut threadedly connected to the threaded plunger rod; an arbor rotatably connected to the dose knob accessible outside the distal end of the chassis, said arbor being connected to the drive nut via an arbor extension, wherein said arbor extension and said arbor are interconnected by second engagement means for providing a rotational lock of the arbor extension in an opposite direction when said arbor is rotated by said dose knob, wherein said arbor extension and said drive nut are interconnected by third engagement means for providing a rotational lock but allowing a longitudinal movement of the drive nut in relation to the arbor extension; spring force means having a first end connected to the arbor and a second end connected to a fixed point on the chassis such that said spring force means is tensioned when said dose knob and said arbor are rotated; guide part arranged with guide ledges which cooperate with longitudinal grooves of the plunger rod for providing a rotational lock but allowing a longitudinal movement of the plunger rod in relation to the guide part.

According to a further aspect of the invention, the activation means is releasable interconnected to said arbor extension by fourth engagement means for providing a rotational locking of the arbor extension in one direction when said arbor is rotated and said spring force means is tensioned, and for releasing said rotational locking when said fourth engagement means are moved away from each other, such that said arbor, said arbor extension and said drive nut are rotated in the opposite direction forcing the plunger rod to move axially exerting pressure on the piston and thereby on the medicament inside the container for expelling a certain predetermined quantity of the medicament through the medicament droplet generator and thereby through the mouth piece.

According to a yet another aspect of the invention, the device further comprises pressure release means comprising slanting wedge-like surfaces arranged on said drive nut and slanting wedge-like surfaces arranged on a fixed inner annular surface of the chassis, which slanting wedge-like surfaces are abutting each other such that they move out of contact near the end of the delivery of the predetermined quantity when the drive nut is rotated for reducing the pressure inside said medicament container at end of delivery.

According to yet a further aspect of the invention, the dose knob and the arbor are releasably connected to each other by sixth engagement means during dose setting and tensioning of said spring force means, and wherein said dose knob is rotationally locked by fifth engagement means when said dose knob and said arbor are disconnected from each other.

According to another aspect of the invention, the rotation damping member is arranged between said arbor and said dose knob capable of damping the initial movement of said arbor during delivery of dose and thereby the initial pressure peak inside said medicament container.

According to a further aspect of the invention, the rotation damping member comprises a proximal part rotationally connected to said arbor and a distal part protruding into a compartment in said dose knob, which compartment is filled with a highly viscous material, wherein said highly viscous material is grease.

According to yet a further aspect of the invention, the proximal end of the mouth engaging area comprises at least one guide means which is/are readily sensed by the lips of a user for ensuring efficient airflow and for positioning the mouth piece at a predetermined distance from the pharynx of a user.

According to another aspect of the invention, the central axis of the mouth piece is in a range of 100-120° in relation to the central axis of the medicament container.

According to yet a further aspect of the invention, the piston is a customized piston comprising a rigid core or the like.

According to yet another aspect of the invention, the chassis and the medicament container holder are releasably connected to each other by first engagement means.

According to yet a further aspect of the invention, the medicament container is a standard and/or standard size medicament cartridge or syringe.

According to a further aspect of the invention, the medicament container is a standard and/or standard size dual chamber cartridge or syringe having two separate components which are introduced to one another by mixing manually or automatically.

According to another aspect of the invention, the device further comprises a handling coordination mechanism capable of coordinating inhalation and delivery of medicament.

According to yet a further aspect of the invention, the handling coordination mechanism comprises a blockage member positioned in said mouth piece, which blockage member is operatively connected to the activation means such that said blockage member is removed from said mouth piece when said activation means is operated.

According to yet another aspect of the invention the handling coordination mechanism comprises an activation blockage mechanism operatively connected to the mouth piece such that said activation blockage mechanism is removed from the activation means during inhalation through said mouth piece.

According to another aspect of the invention, said spring force means is a pre-tensioned spiral strip drive spring.

There are several advantages with the present invention. The use of a pressure reducing function at the end of the medicament delivery phase, a very reduced risk of drooling is obtained in that the pressure inside the medicament container is drastically and steeply reduced. Especially with droplet inhalers producing very small droplets through the plurality of orifices by the highly pressurised medicament liquid forced through the orifices, it is important that the pressure is cut off as fast as possible, otherwise the medicament liquid will not form droplets by will just drip from the medicament droplet generator. On the one hand this fouls or contaminates the device and in particular the mouth piece, but there is also a risk that the orifices are clogged and blocked by the dripping or drooling medicament. The problem with drooling is further pronounced when the medicament liquid is highly viscous, thus displaying resilient properties that enhance the drooling.

In order to further control the pressure inside the medicament container during medicament delivery, a dampening member is used initially. It effectively reduces the initial peak force and thus peak pressure, which peak pressure reduction also reduces the risk of breaking components of the device.

With these measures initially and at the end of delivery as well as utilising a spiral strip drive spring that is pre-tensioned before setting a dose and further tensioning the spring, a very controlled and nearly constant pressure curve is produced during the whole medicament delivery phase, which is very beneficial for the production of small droplets of medicament throughout the whole phase.

The device may advantageously be in two inter-connectable parts such that a new medicament container may replace a used container.

In order to further the proper administration of medicament into the lungs of the user, a handling coordination mechanism may be introduced. It preferably inter-connects the mouth piece with the activation means such that it either is not possible to inhaler until the device is activated, or that it is not possible to activate the device until the user inhales. This reduces the risk that the device delivers a dose when the patient is not inhaling, thereby reducing the risk of contaminating the device with medicament.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

As used herein, the term "liquid" encompasses all solutions, suspensions, emulsions, oils, gels and so forth which generally behave as liquids at operating temperatures. The term explicitly includes solid compositions dissolved or dispersed in a liquid carrier. Materials behaving as highly viscous liquids are also included.

In the present application, when the term "distal part/end" is used, this refers to the part/end of the medical delivery device, or the parts/ends of the members thereof, which under use of the device is located the furthest away from the delivery site of the patient. Correspondingly, when the term "proximal part/end" is used, this refers to the part/end of the device, or the parts/ends of the members thereof, which under use of the device is located closest to the delivery site of the patient.

Figure 2:
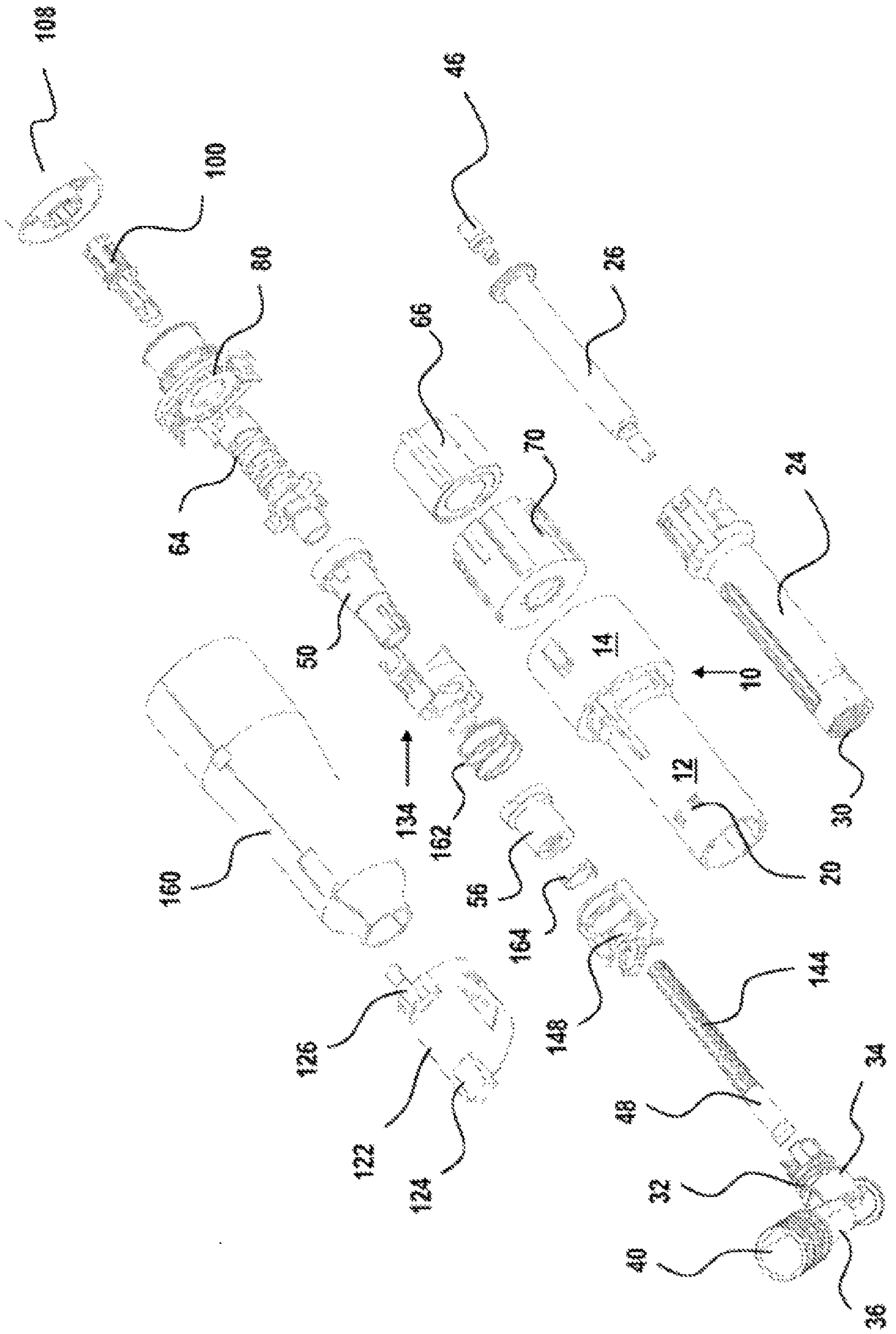
FIG. 2 is an exploded view of the device of FIG. 1, FIGS. 3*a, b* are detailed views of a chassis comprised in the present invention, where 3*b* is turned 180°.
Figure 3B:
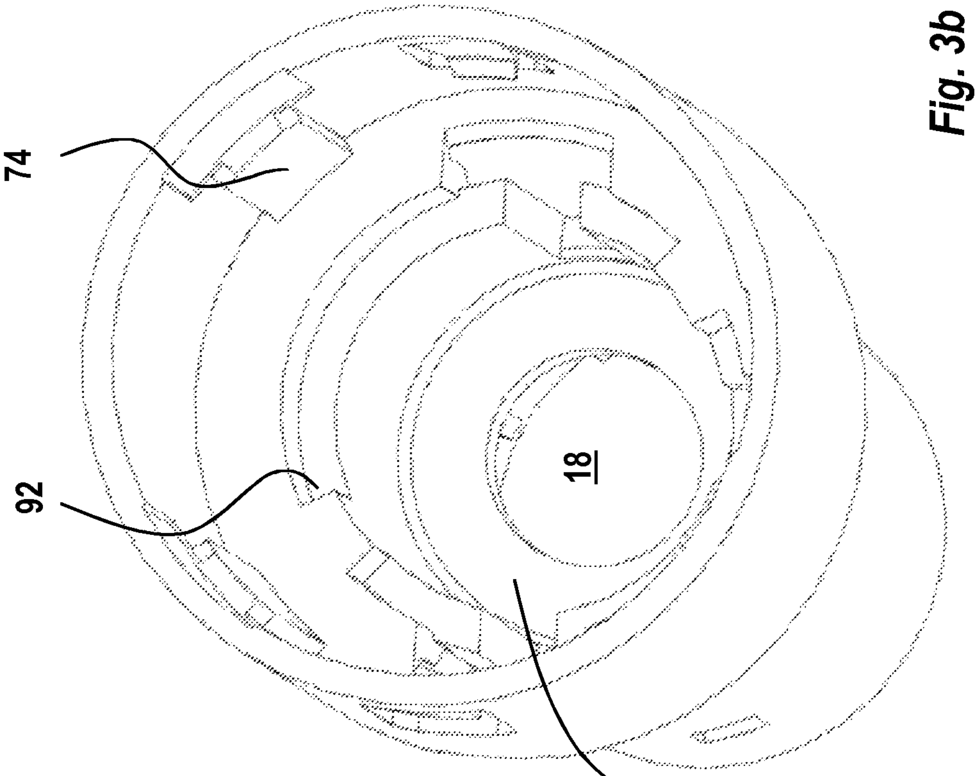
Figure 3A:
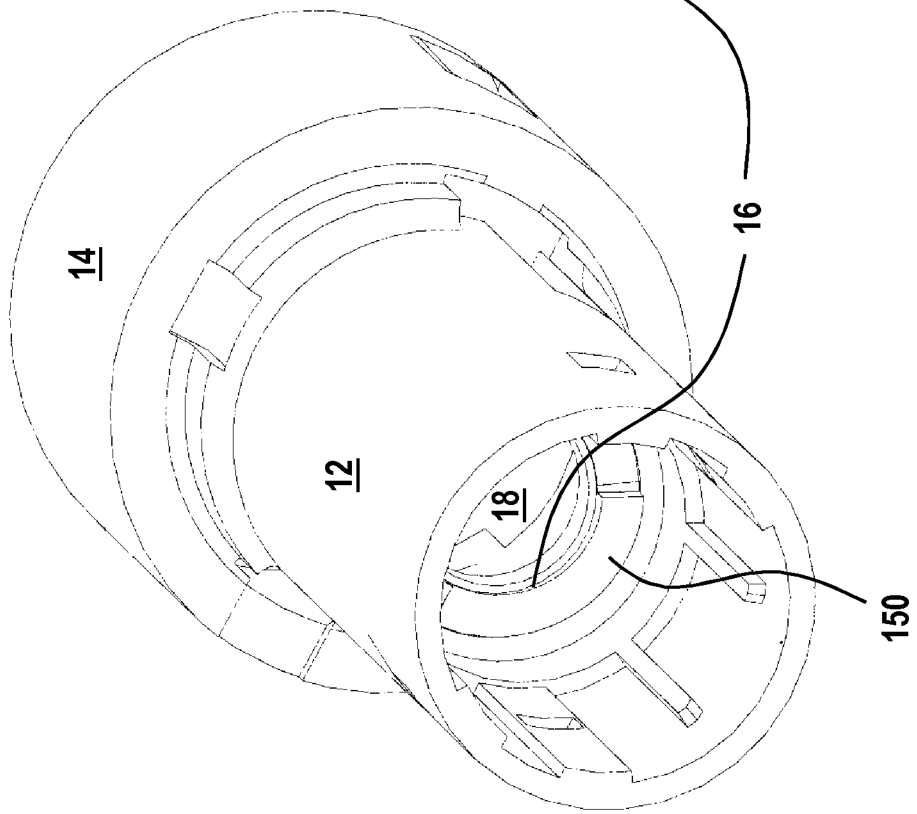

The device according to the present invention shown in the drawings comprises a main chassis 10 in the form of a generally elongated tubular body having opposite proximal and distal ends, where the proximal part 12, FIG. 2, has one diameter and the distal part 14 has a somewhat larger diameter. A transversal interior wall 16, FIG. 3, is positioned in the transition between the proximal part 12 and the distal part 14, further provided with a central passage 18. The proximal part 12 of the chassis is arranged with passages 20 on the side surface, which passages 20 are releasably arranged to interact with protrusions 22, FIG. 4, forming first engagement means, arranged on an outer surface of a distal area of a generally tubular, elongated, medicament container holder 24 such that the two parts may be attached to each other. Inside the medicament container holder 24 a medicament container 26 can be positioned.

Figure 4:
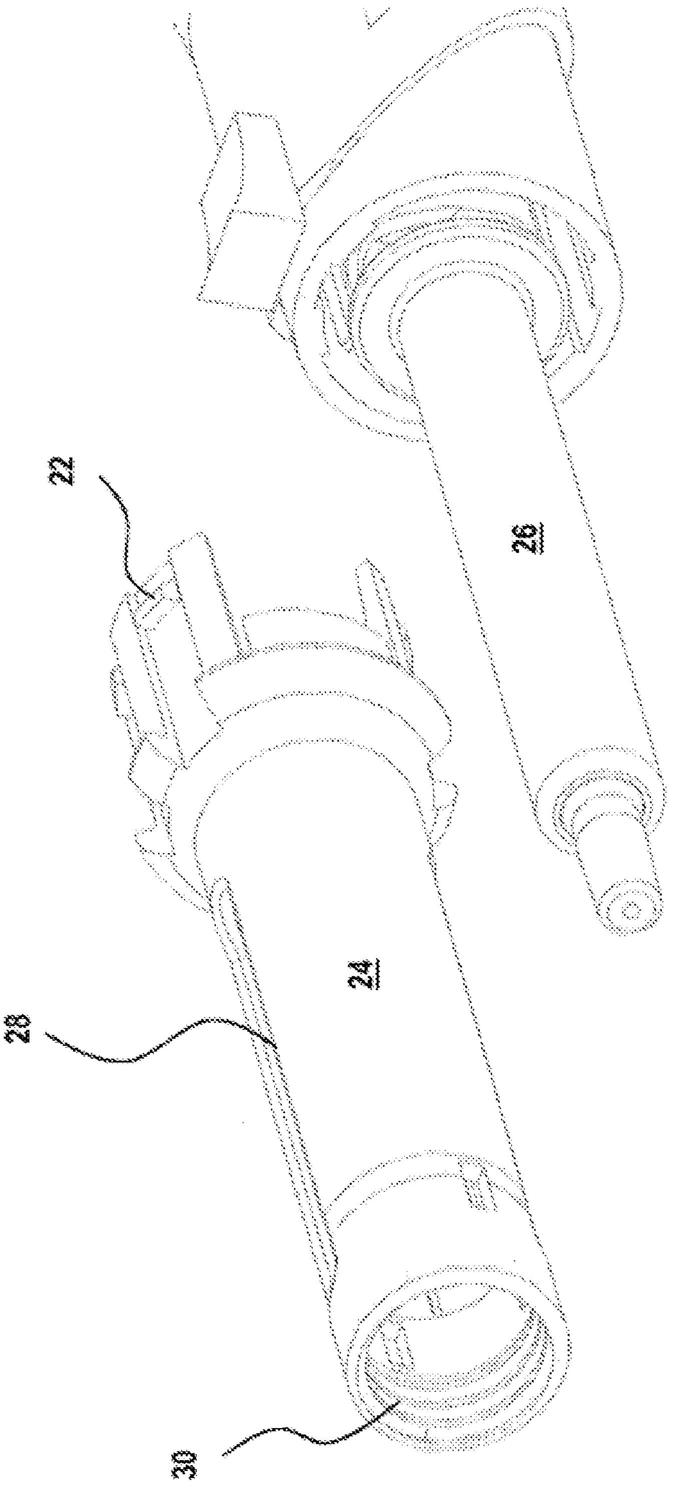
FIG. 4 is a detailed view of a proximal part of the device.

The medicament container and its content are visible through an opening or window 28 in the medicament container holder, FIG. 4. However, for some types of light sensitive medicaments, the glass may be tinted, coated or opaque. Moreover, the container holder may also be made of a transparent material. Preferably the medicament container 26 is a standard and/or standard size cartridge or syringe, readily available on the market in a number of dimensions depending on the application. The medicament container comprises a tubular form having at least one chamber capable of containing a composition, a proximal opening for allowing the composition to be expelled therefrom, and at least one axially movable piston 42, e.g. a rubber stopper. The proximal end of the medicament container holder 24 is arranged with threads 30 on its inner circumferential surface, FIG. 4. These threads 30 cooperate with corresponding threads 32 on an attachment part 34 of mouth piece 36, FIG. 2.

A general discussion of the mouthpiece for an inhaler device is found in WO 06/094796, for example ranges of dimensions and configurations which may be adopted to achieve a desired particle size and flow pattern. As such, the disclosure of WO 06/094796 is incorporated by reference herein.

A component of the inhaler device of the invention is a droplet generator 38 that interfaces with an airflow which is generally perpendicular to the direction of droplet travel at expulsion from the droplet generator. This helps ensure the droplets remain the desired size and dispersed within the air flow.

The mouth piece 36 is designed with a generally tubular shape comprising a mouth engaging area and an air opening, wherein the proximal end of the mouth engaging area comprises at least one guide means as e.g. at least three spaced concentric rings which are readily sensed by the lips of a user. In such a design, the mouth engaging area helps a user seal their mouth around the mouth piece to ensure efficient airflow, but also positions the mouth piece at a predetermined distance from the pharynx of a user.

When a user places the mouth piece in their mouth and sealingly locates their lips around mouth engaging area, inhaled air towards the users mouth travels through the mouth piece via the air opening. The air opening forms the opposite end of the mouth engaging area. Alternative embodiments are possible, for example a plurality of openings along the cylindrical surface near the proximate end.

A determining factor in the design and placement of the air opening is that it has to be proximate to the droplet generator as the air inspired through the opening is to carry the droplets into the mouth of a user. Furthermore, an air flow which is generally perpendicular to the direction of travel of the generated droplets is effective in ensuring droplets remain discrete and well distributed in the airflow.

A droplet access opening is provided in the mouth piece. The droplet access opening may incorporate the droplet generator 38, or may be located adjacent to the droplet generator.

Figure 1:
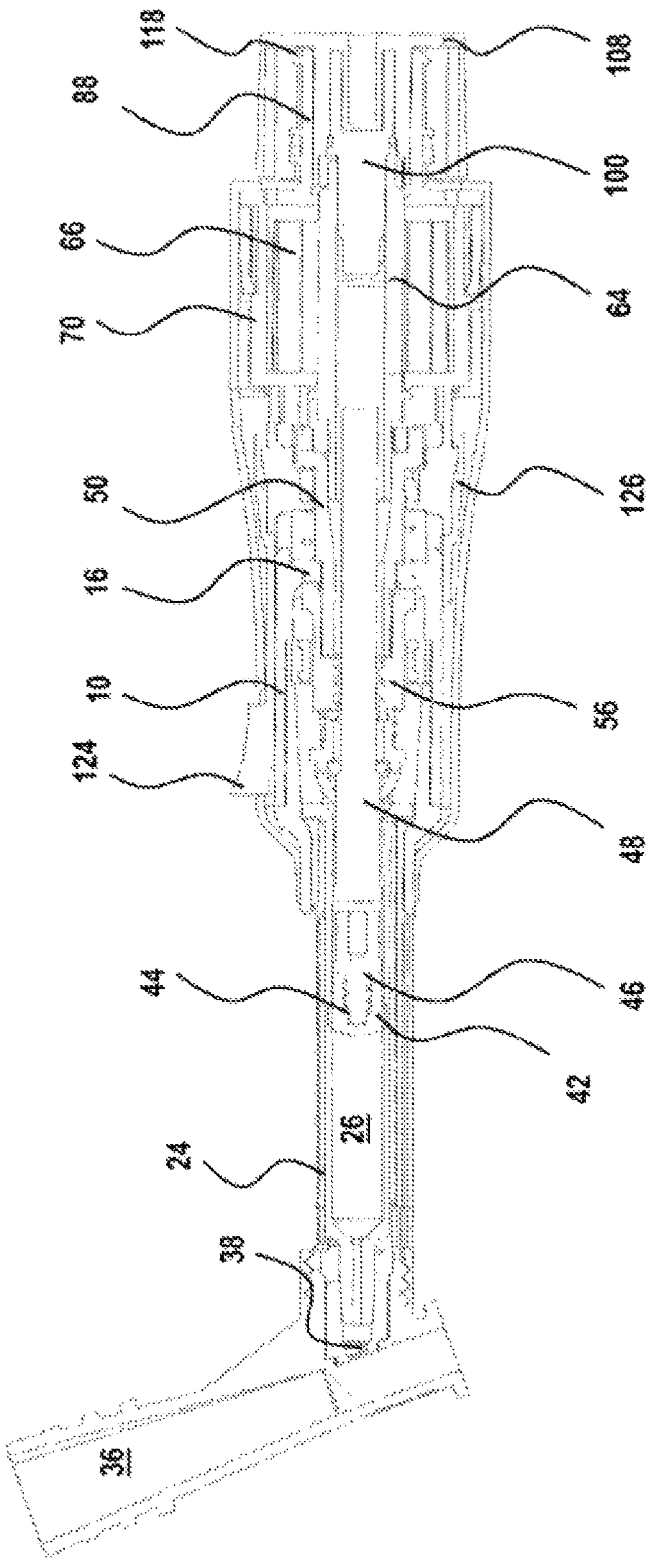
FIG. 1 is a cross-sectional side view of a device according to the present invention.

In FIG. 1, the central axis of the mouth piece is not perpendicular to the central axis of the container but instead at an angle of greater than 90°. The angle at which the mouth piece may be provided relative to the container can be in a range of about 90° to 180°. To maximize the amount of composition bypassing the mouth and entering the airway a range of about 100-120° may be preferred. As the angle approaches 90° the amount of composition deposited on the tongue can increase. This can be particularly undesired where the composition has an unpleasant taste.

The mouth piece may be a replaceable component of the device, that is, discarded with each refill or resupply of composition to the device, alternatively the mouth piece may be reusable. Where reuse is intended, it can easily be cleaned or sterilised.

The medicament droplet generator is of a type working with a very large number of very small orifices, through which the liquid medicament is forced and atomised. One type of such a medicament droplet generator that may be utilised is described in document WO 02/18058, which discloses a micro-machined medicament droplet generator plate that may produce small liquid droplets in air with a narrow droplet size distribution. The size of the delivery end 40 and corresponding size of the medicament droplet generator may be varied depending on the particular application. It is also conceivable that the medicament droplet generator may be replaceable and made in any suitable material such as glass, plastics and silicone, as well as a mix of different materials.

WO 02/18058 reiterates the value of an atomisation droplet generator capable of producing droplets having a narrow size distribution. Furthermore, the nozzle of WO 02/18058 can be employed to produce mists as well as oil in water or water in oil emulsions. The disclosure of WO 02/18058 may serve as a useful reference for a skilled worker practicing the present invention and as such its contents are herein incorporated by reference. Further general details of droplet generators are described in WO 09/002,178 which is herein incorporated by reference.

Optionally, the droplet generator 38 can be provided as part of the proximal end of the medicament container, wherein the desire for ease of manufacture and the expected degree and type of re-use of the device are to be taken into account.

The device also comprises a power supply mechanism comprising a threaded plunger rod 48, a drive nut 56, an arbor 64, an arbor extension 50, spring force means 66, and a guide part 152.

The stopper 42, when using standard and/or standard size cartridges or syringes, is often designed with a central recess 44 facing in the distal direction and in order not to collapse the stopper 42 during high forces, a so called plunger support 46 is arranged to fit into the recess of the stopper. It is also conceivable to have a customized stopper as e.g. a stopper comprising a rigid core or the like. Further the elongated threaded plunger rod 48 is arranged in contact with the plunger support 46 with its proximal end.

Figure 5:
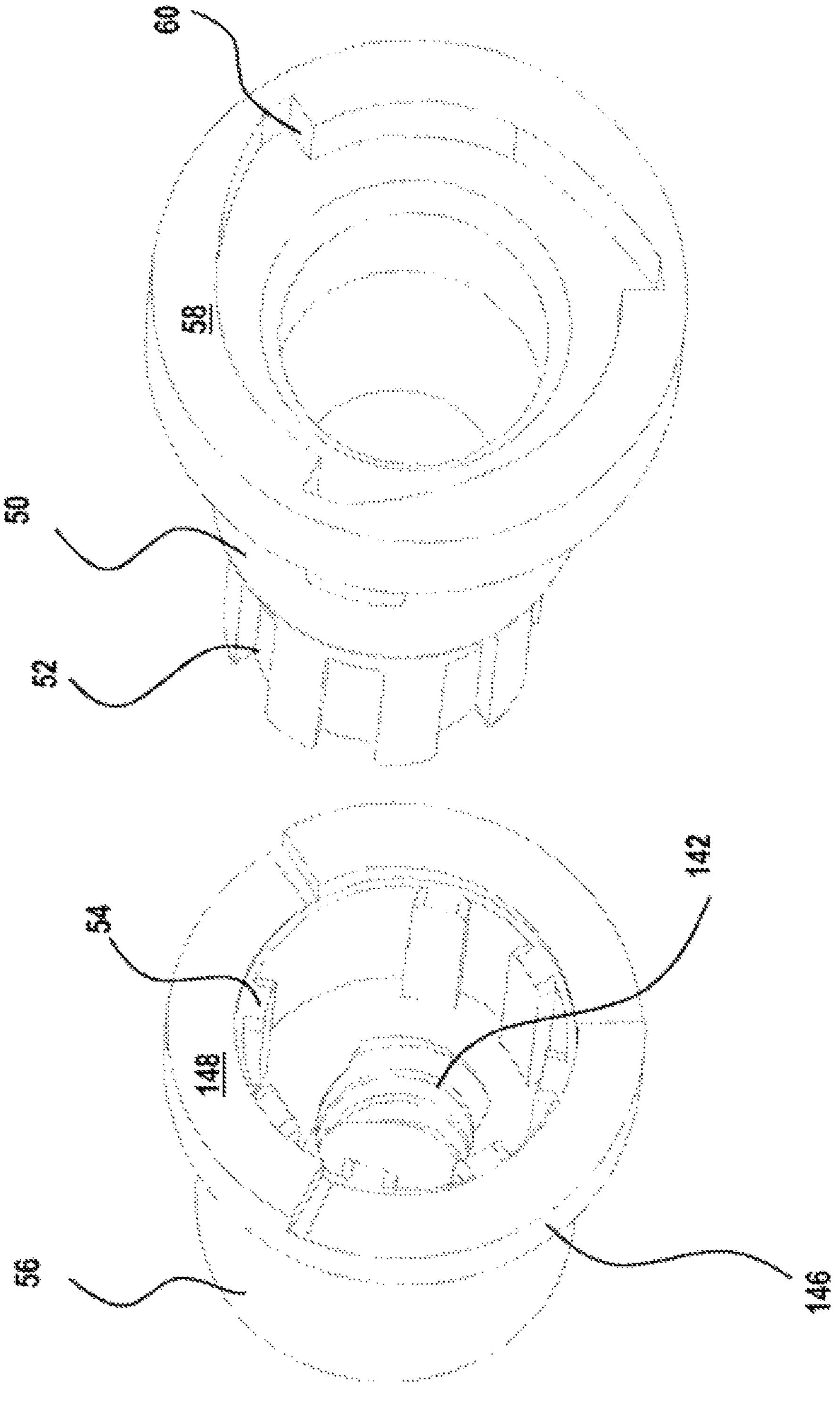
FIG. 5 is a detailed view of a drive nut and of an extension arbor comprised in the device according to the present invention.
Figure 6:
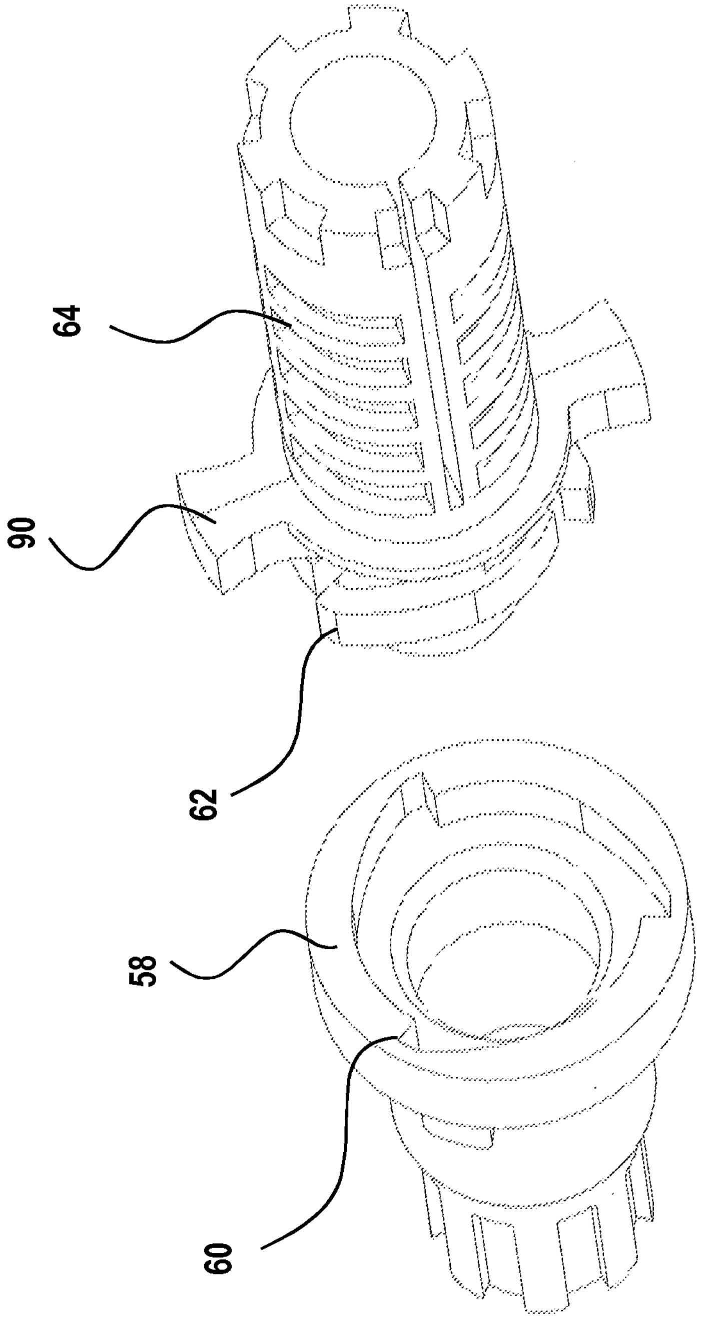
FIG. 6 is a detailed view of an arbor and of the extension arbor comprised in the device according to the present invention.

The plunger rod 48 is arranged inside a so called arbor extension 50 having a generally tubular shape, FIGS. 2 and 5. A proximal end part of the arbor extension 50 is arranged with spline grooves 52 on its outer surface. The spline grooves 52 mate with corresponding spline ridges 54 on an inner surface of a generally tubularly shaped drive nut 56 forming a third engagement means, FIG. 5. Further, the arbor extension 50 is arranged with a ring-shaped part 58, where the inner surface of the ring 58 is arranged with transversal stop ledges 60. These stop ledges 60 cooperate with flexible arms 62 of an arbor 64, FIG. 6, forming a second engagement means.

However the stop ledges 60 and flexible arms 62 are arranged such that the arbor 64 may only be rotated in one direction in relation to the arbor extension 50, where the flexible arms 62 slide over the stop ledges 60. In the other direction, the ends of the flexible arms 62 abut the stop ledges 60, thereby blocking the rotation.

Figure 7:
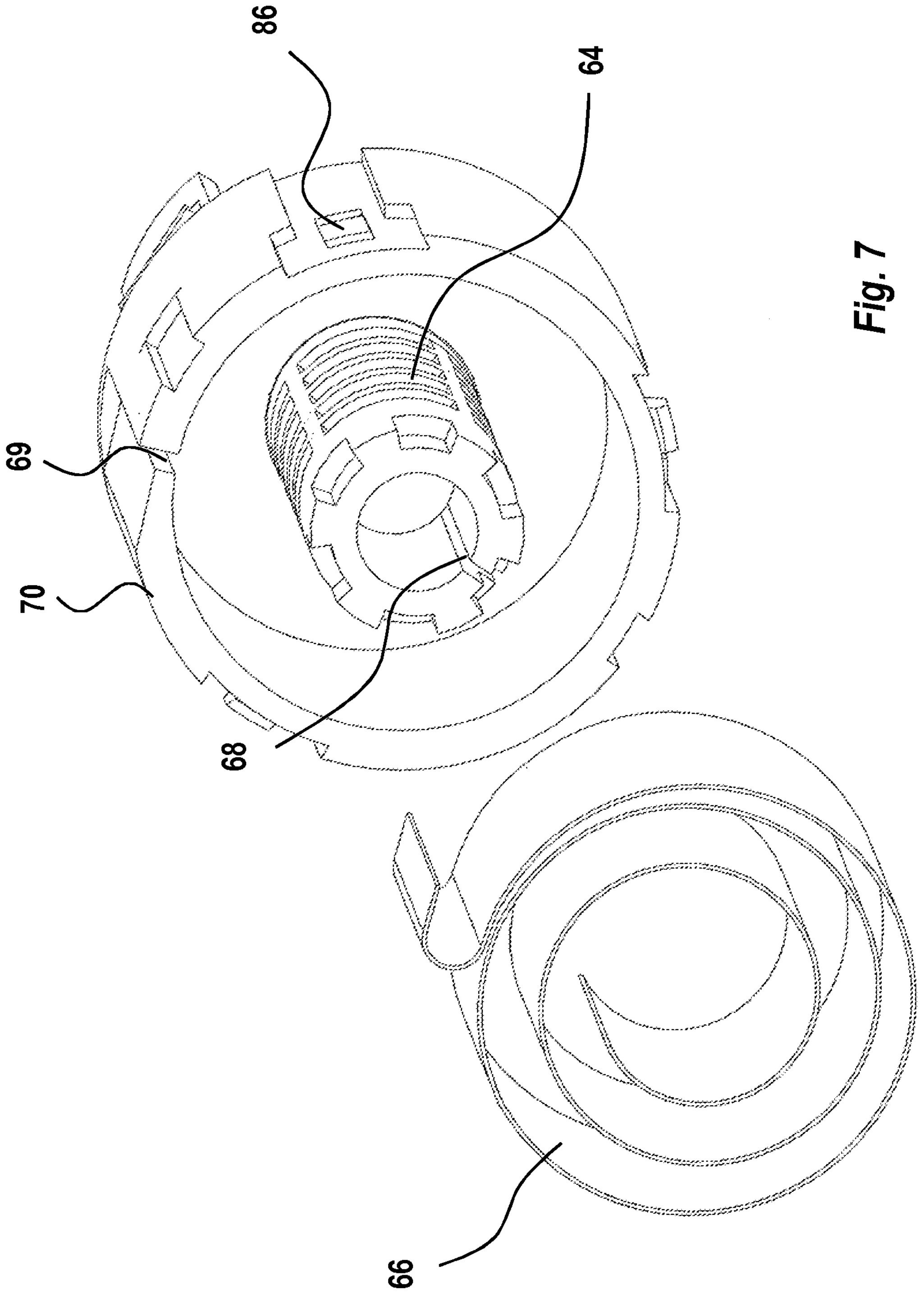
FIG. 7 is a detailed view of a house and of a spring force means comprised in the device according to the present invention.

The spring force means 66 as e.g. a spiral strip drive spring is arranged around the arbor 64 and attached with one end in an elongated slit 68 in the arbor 64 and with the other end in a slit 69 in a house 70, FIG. 7. The house 70 is in turn placed inside the distal part of the chassis 10 and held fixed in relation to the chassis 10 by longitudinal grooves 72 fitting with corresponding ridges 74, FIGS. **3*b* and 7. The house 70 is held in place by inwardly protruding flexible arms 76 fitting into corresponding grooves 78, FIGS. 3*b* and 7. The house 70 is connected to a house cover 80 by proximally directed arms 82 with passages 84, into which ledges 86 on the outer surface of the house 70 fit, FIG. 8, such that when assembling the house 70 and the house cover 80 to the chassis, the arms 82 are prevented to flex radially outwards. The house cover 80 is further arranged with a distally directed tubular member 88, FIG. 8**.

The arbor 64 is further arranged with two stop ledges 90 co-acting with corresponding stop ledges 92, FIGS. **3*b* and 6, arranged in the interior of the chassis 10 for limiting the rotation of the arbor 64, as will be described. The distal end of the arbor 64 extends into the tubular member 88 of the house cover 80. The distal end of the arbor 64 is also arranged with a central passage 94, FIG. 8, which passage 94 is arranged with spline grooves 96**.

The device further comprises a rotation damping member 100 comprises a proximal part rotationally connected to the arbor whereby the spline grooves 96 are cooperating with splines 98 on the proximal outer surface of said rotation damper member 100.

Figure 8:
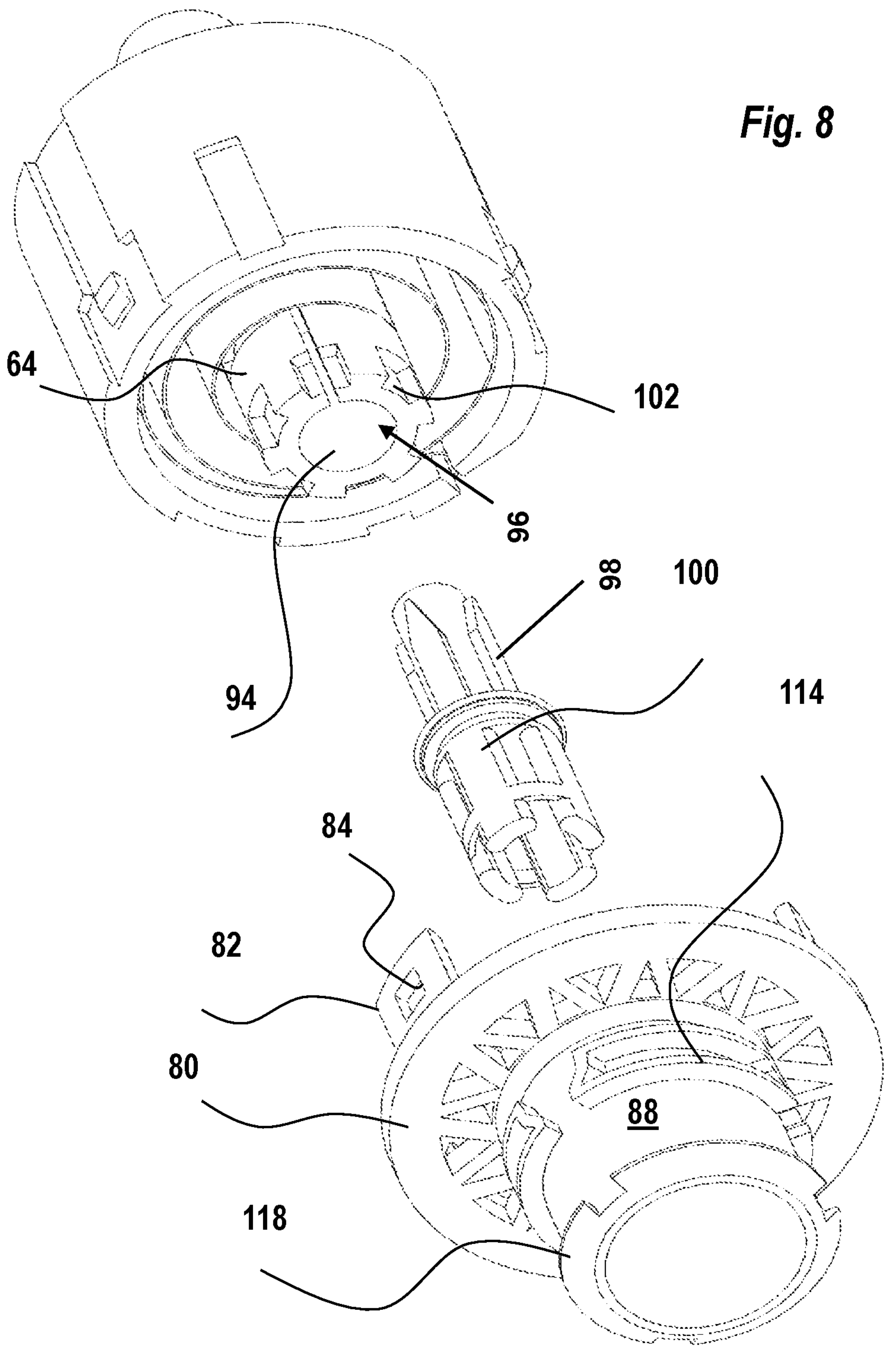
FIG. 8 is a further detailed view of the house, of a house cover and of a rotation damping member comprised in the device according to the present invention.
Figure 9:
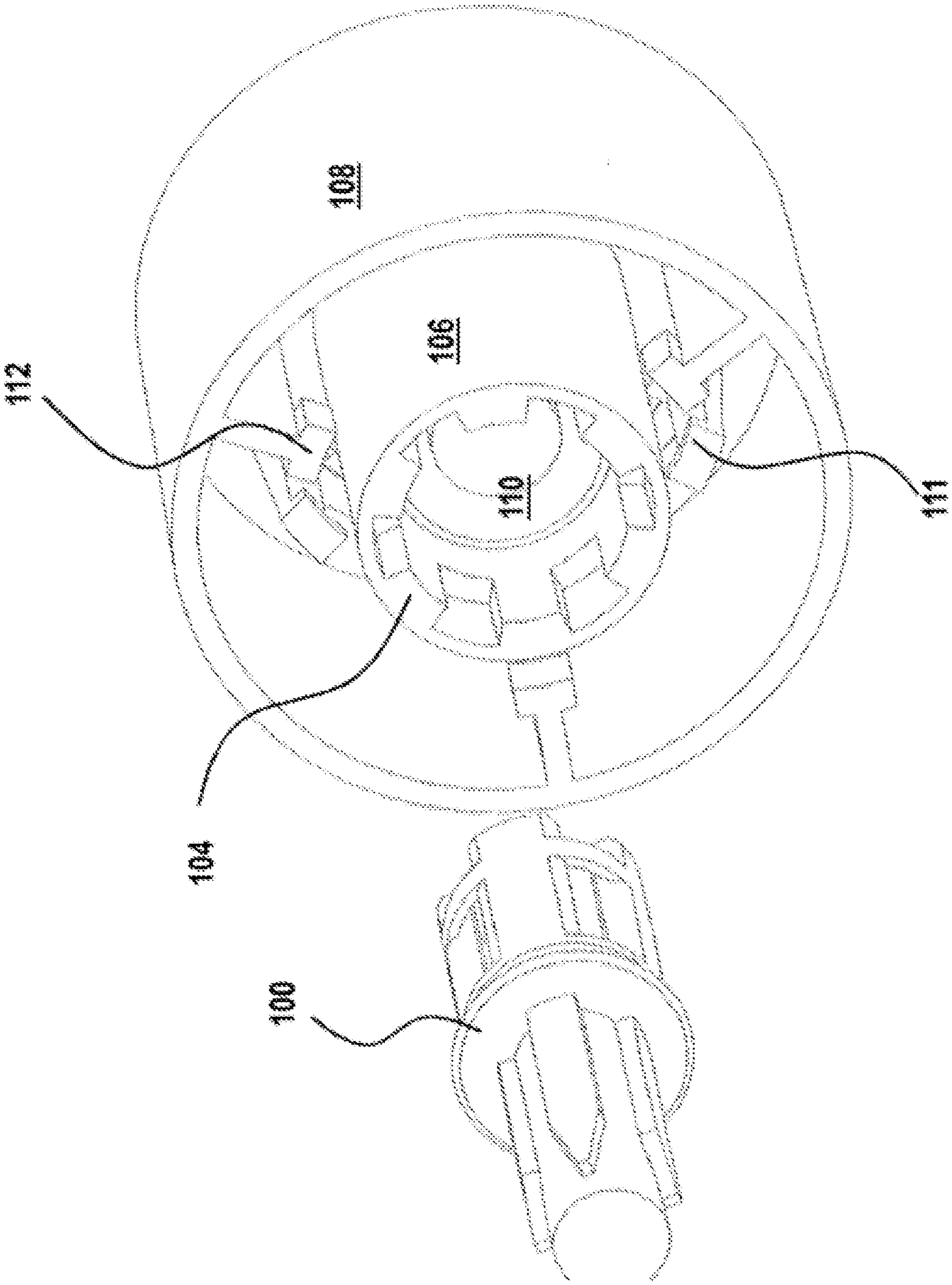
FIG. 9 is a detailed view of the rotation damper member and of a dose knob comprised in the device according to the present invention.

The rotation damping member 100 also comprises a distal part protruding into a compartment 110 of the central tubular member 106 and the space between the rotation damper member 100 and the inner surface of the tubular member 106 is filled with a high viscous material as e.g. grease, FIGS. 8 and 9. The arbor 64 is further arranged with spline grooves 102 on its outer surface in the distal area, FIG. 8. These spline grooves 102 cooperate with corresponding ridges 104 arranged in a central tubular member 106 of a dose knob 108, FIG. 9, forming a sixth engagement means. The dose knob 108 is further arranged with radially inwardly directed ledges 112 adjacent its proximal end surface. The ledges 112 cooperate with ridges 114 on the outer surface of the tubular member 88 of the house cover 80, FIGS. 8 and 9, as to allow certain movement patterns as will be described below. The dose knob 108 is arranged with further inwardly directed ledges on 111 its inner surface in the distal area, which ledges 111 cooperate with an annular ledge 118 at the distal end of the tubular member 88 of the house cover 80. Moreover, it is also conceivable that the dose knob and the tubular member comprise other forms of cooperating means. Further a spring (not shown) is arranged between the house cover 80 and the dose knob 108 for urging the latter in the distal direction. When in this position, the dose knob 108 is disconnected from the arbor 64, i.e. there is no connection by the sixth engagement means 102, 104.

Figure 10:
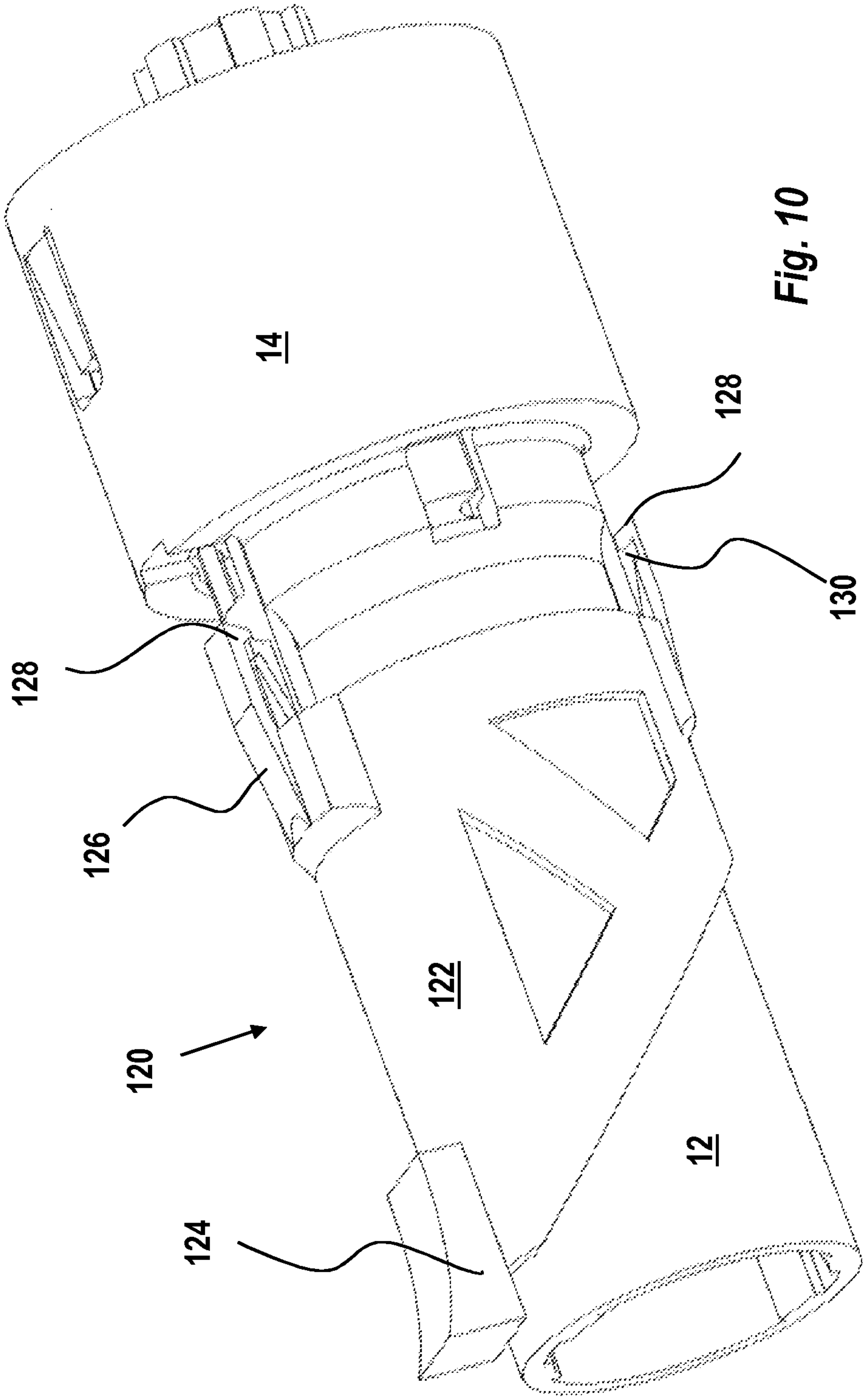
FIG. 10 is a detailed view of the chassis connected to an activation means comprised in the device according to the present invention.

Further, the device comprises activation means 120, FIG. 10, arranged slidable with a sleeve-like member 122 surrounding the chassis 10 and with a button 124 protruding radially. The distal end of the sleeve member 122 is arranged with distally directed tongues 126, which tongues 126 are provided with inwardly directed ledges 128. These ledges 128 grip around outwardly directed ledges 130 arranged on longitudinally extending arms 132 of a dose activator 134, FIG. 11 The dose activator 134 has a ring-shaped body 136 on which the arms 132 are attached. Further, the centre surface of the ring-shaped body 136 is arranged with radially directed stop ledges 138 cooperating with stop ledges 140 on the outer surface of the arbor extension 50, forming a fourth engagement means. It is also conceivable that the activation means are breath activated means as disclosed in the patent EP1225942B1, incorporated by reference herein.

The inner surface of the drive nut 56, FIG. 5, is further provided with threads 142 which cooperate with threads 144 on the outer surface of the plunger rod 42. The drive nut 56 is further arranged with an annular ledge 146 with a distally directed end surface having a number of slanting wedge-shaped surfaces 148, the function of which will be described below. The proximally directed surface of the interior wall 16 of the chassis 10 of the device is arranged with corresponding slanting wedge-shaped surfaces 150. A return spring 162 is arranged between the distally directed surface of the interior wall 16 of the chassis 10 and the proximally directed surface of the ring-shaped body 136 of the dose activator 134, FIG. 2, the function of which will be explained below.

Figure 12:
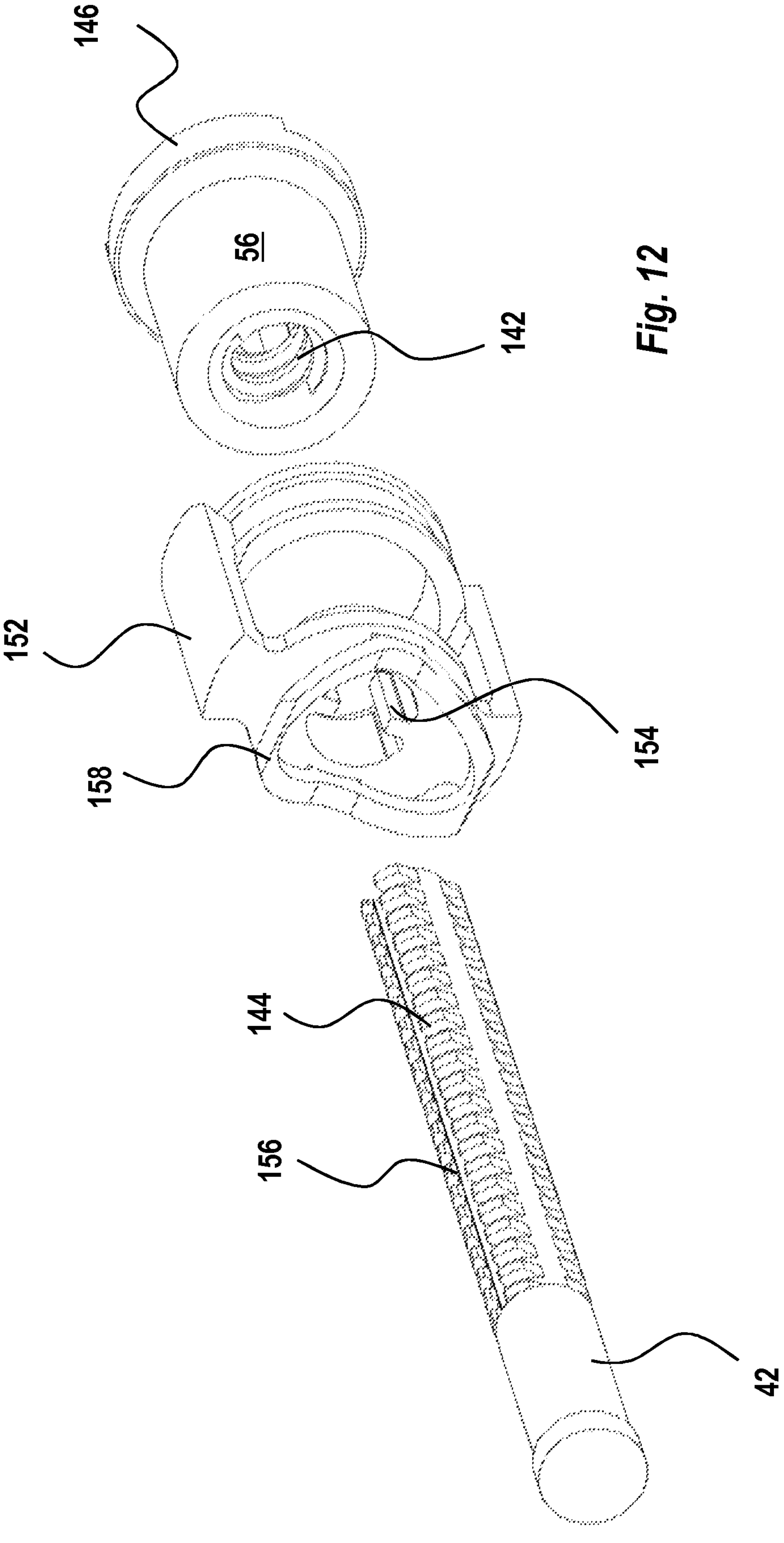
FIG. 12 is a further detailed view of the drive nut, of a guide part and of a plunger rod comprised in the device according to the present invention, FIGS. 13*a, b* is a detailed view of a first handling coordination mechanism.

The plunger rod 42 is further arranged through the guide part 152, FIG. 12, which is rotationally lockable with the chassis 10 when the medicament container holder is connected to the chassis 10, but the guide part can be rotated when the medicament container holder is not connected to the chassis. The guide part 152 is arranged with guide ledges 154 which cooperate with longitudinal grooves 156 of the plunger rod 42, providing a rotational lock but allowing a longitudinal movement of the plunger rod 42 in relation to the guide part 152. The proximal end surface of the guide part 152 is provided with flexible ring-shaped members 158, which come in contact with the distal end surface of the medicament container 26 when assembled, thereby pushing the medicament container 26 in the proximal direction. Further the device is covered by an appropriately designed casing 160 attached to the chassis 10 either fixed or removably, depending on the application.

The device is intended to function as follows. A medicament container 26 is placed in the medicament container holder, which then is engaged to the chassis 10, whereby the guide part 152 becomes rotationally locked by suitable engagement means on the chassis and/or the container holder. The casing 160 is then attached to the chassis 10 and medicament container holder.

When a dose is to be set the dose knob 108 is to be rotated. In order to connect the dose knob 108 to the dose setting mechanism, the dose knob is pushed in the proximal direction. The dose knob 108 and the arbor 64 are then connected by the sixth engagement means 102,104. Thus when the dose knob 108 is rotated, the arbor 64 is also rotated. The rotation of the arbor causes the spiral strip drive spring 66 to be further tensioned from an initial state where the spring is already pre-tensioned and whereby a rotational force is accumulated.

During rotation of the arbor 64, the flexible arms 62 move out of contact with the stop ledges 60 of the ring-shaped member 58 of the arbor extension 50 until they are moved in contact with subsequent stop ledges 60. The arbor 64 is prevented from being rotated back because the contact of the flexible arms 62 with the stop ledges 60 of the arbor extension 50, FIG. 6. The arbor extension is prevented from rotating due to the connection between the spline grooves 52 with the corresponding spline ridges 54 on the inner surface of the drive nut 56, and the drive nut is prevented from rotation due to the connection between the slanting wedge-shaped surfaces 148 of the drive nut 56 and the slanting wedge-shaped surfaces 150 on the interior wall 16 of the chassis 10.

Figure 11:
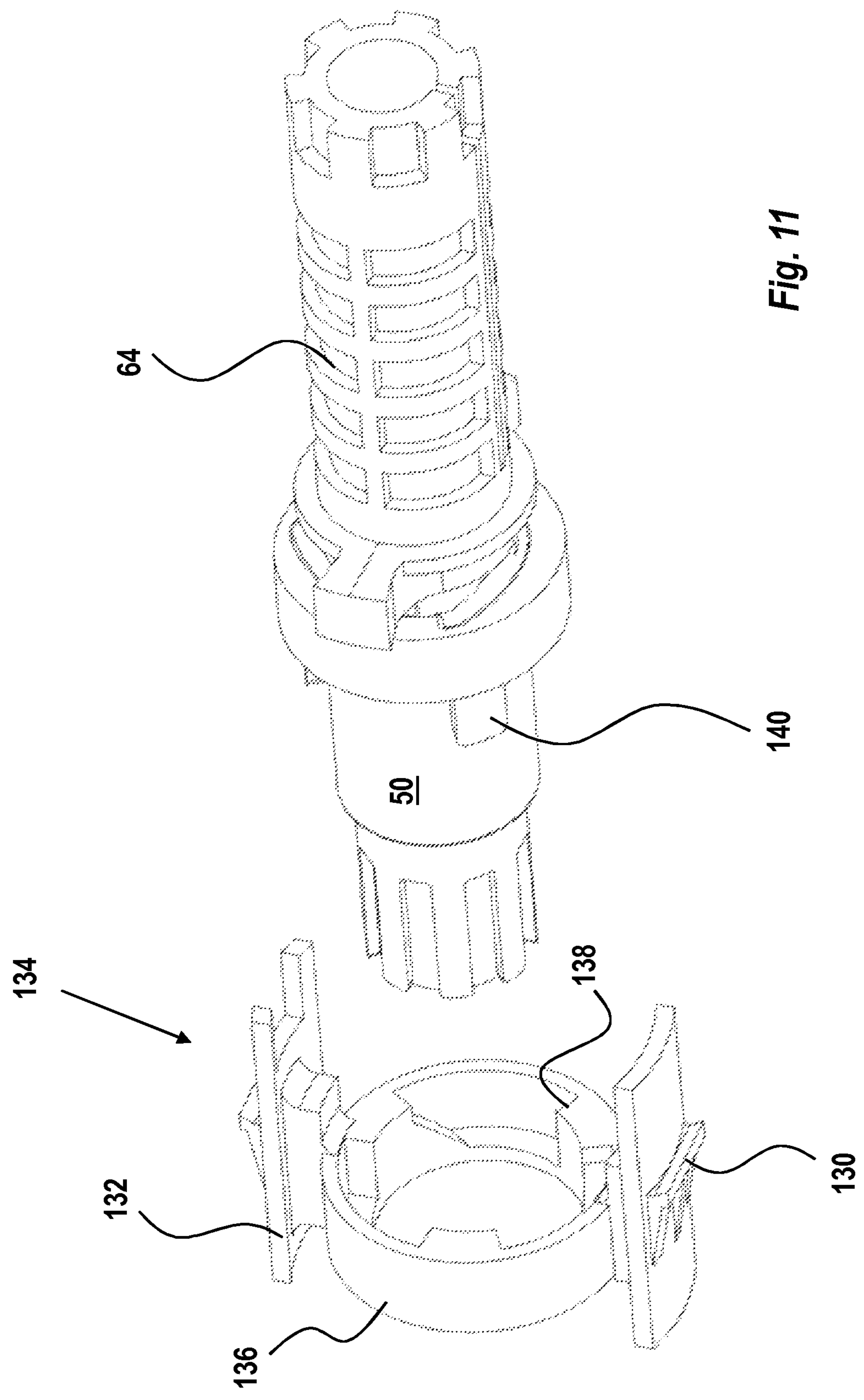
FIG. 11 is a further detailed view of the arbor connected to the arbor extension and of a dose activator comprised in the device according to the present invention.

Further, the arbor extension 50 is in turn prevented from rotating because the wedge-shaped stop ledges 138 of the dose activator 134 are in contact with the stop ledges 140 on the arbor extension, FIG. 11. The dose knob 108 is rotated until the stop ledge 90 of the arbor 64 comes in contact with the corresponding stop ledge 92 of the chassis 10, FIGS. 3*b* and 6. This ensures that the user cannot turn the dose wheel beyond a preset position, and thus that a too large dose cannot be set. In the embodiment shown, the dose knob and thus the arbor can be turned 120 degrees for setting a dose. Because of this, the flexible arms 62 together with the stop ledges 60 are three and have a pitch of 120 degrees. The pitch of 120 degrees is also used for the wedge-shaped surfaces 148 of the drive nut 56, FIG. 5, as well as the wedge-shaped surfaces 150 of the chassis wall 16, FIG. 3*a*. It is to be understood that pitches other than 120 degrees can be used, depending on the dose size and/or the design of other components such as the pitch of the threads 144 of the plunger rod 48 and drive nut 56. When the user releases the dose knob 108 it is moved distally and returned to its initial position where it is locked from rotation by the ledges 112 fitting into the pockets formed by the ridges 114 of the tubular part 88 of the house cover 80 forming a fifth engagement means and the dose knob 108 is again disconnected from the arbor 64, FIGS. 8 and 9.

The user now positions the inhaler at the delivery site and activates the inhaler by sliding the activation button 124 and the sleeve-like member 122 in the proximal direction against the force of the return spring 162. Because of the connection between the sleeve-like member 122 and the dose activator 134, the latter is also moved in the proximal direction. This causes the stop ledges 138 of the dose activator to move out of contact with the stop ledges 140 of the arbor extension 50, FIGS. 10 and 11. The arbor extension 50 and thereby the arbor 64, because of the connection between the flexible arms 62 and the stop ledges 60, are now free to rotate by the force of the spring 66, and due to the splines connection between the arbor extension 50 and the drive nut 56, the latter is also rotated.

Because the arbor 64 rotates, so does the rotation damper member 100 inside the tubular part 106 of the dose knob 108. Due to the grease inside the compartment in which the rotation damper member rotates, a dampening effect is obtained, which reduces the pressure peak inside the medicament container at the start of the medicament delivery.

The accumulated rotational force of the spring is converted into an axial force because of the rotation of the drive nut 56, which is in threaded engagement with the threads 144 of the plunger rod 48, and because of the rotational lock of the plunger rod with the guide part 152, the plunger rod 48 is axially advanced, which causes it to move the stopper 42 and to force the medicament through the nebulising medicament droplet generator 38, whereby very small droplets of medicament are formed. These droplets enter the mouth piece and are inhaled into the lungs by the user.

During the rotation of the drive nut 56, the slanting, wedge-like surfaces 148 of the drive nut 56 will slide on the corresponding wedge-like surfaces 150 of the chassis 10, which causes the drive nut 56 to move axially in the proximal direction, which is allowed by the splines connection with the arbor extension 50. The wedge-like surfaces 148, 150 of the drive nut 56 and the chassis respectively are designed such that there is an abrupt ending of the wedge-shape just before the end-of-dose movement.

The abrupt ending causes the drive nut 56 to move somewhat in the opposite direction, i.e. the distal direction, whereby the plunger rod 48 also is moved in that direction. This movement of the plunger rod effectively releases the pressure that the plunger rod is exerting on the stopper and thus on the medicament in the container. Because of the removal of the pressure, drooling from the nebulising medicament droplet generator after performed delivery is to a large extent avoided. In order to increase the abrupt ending motion, a spring 164 may be arranged between the drive nut 56 and the guide part 152, FIG. 2, capable of urging the drive nut 56 towards the distal end of the device.

The delivery device can now be removed from the delivery site. For subsequent delivery, where a multi-dose container is used, the dose knob 108 is rotated to set the dose and tension the spring. When the multi-dose container is empty, or if a single-dose container is used, the proximal medicament container holder 24 is detached from the chassis 10 and the medicament container 26 is removed. The now proximally advanced plunger rod may be moved back in its original position, which is allowed since the guide part 152 now is free to rotate, whereby the plunger rod 48 also can be rotated. A new container is placed in the proximal housing part, after which the latter is again connected to the distal housing part.

According to the invention, emulsions in, for example, water or saline, could be administered. For such applications, the composition could be provided as two separate components which are introduced to one another and mixed manually or automatically e.g. by having at least one extra plunger rod coaxially arranged inside the threaded plunger rod. The disclosure of EP1542744B1 may serve as a useful reference for a skilled worker practicing the present invention and as such its contents are herein incorporated by reference. The mixing can also be manually achieved by e.g. an axially displacement of the medicament container holder into or onto the chassis.

FIGS. 13-17 show different solutions regarding a handling coordination mechanism capable of coordinating inhalation and delivery of medicament, wherein said handling coordination mechanism comprises a blockage member positioned in said mouth piece, which blockage member is operatively connected to the activation means such that said blockage member is removed from said mouth piece when said activation means is operated. Alternatively, said handling coordination mechanism comprises an activation blockage mechanism operatively connected to the mouth piece such that said activation blockage mechanism is removed from the activation means during inhalation through said mouth piece.

Figure 13B:
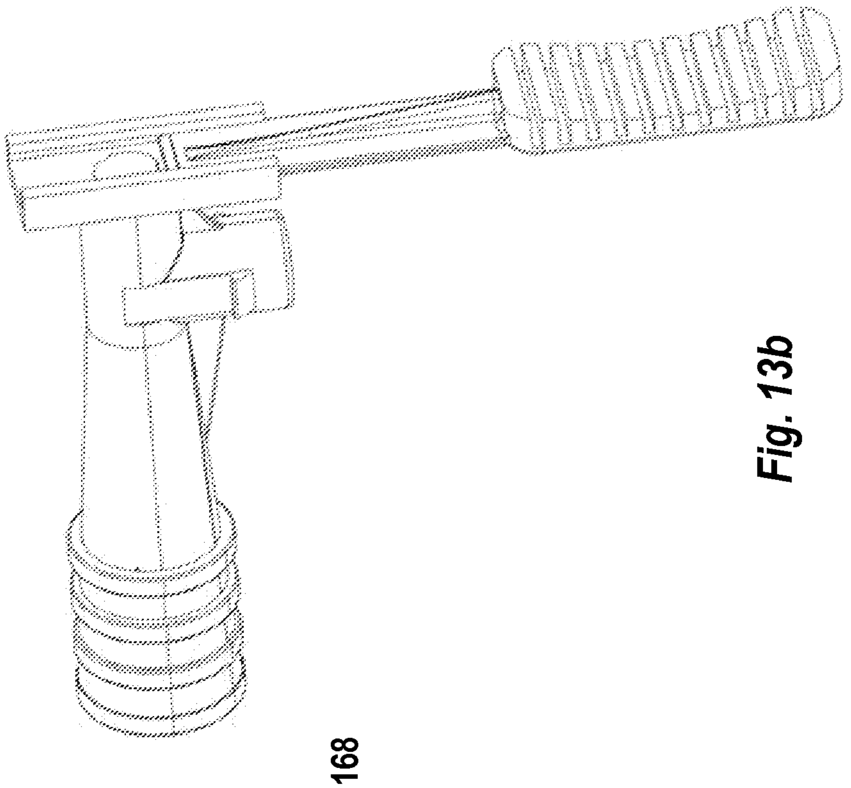
Figure 13A:
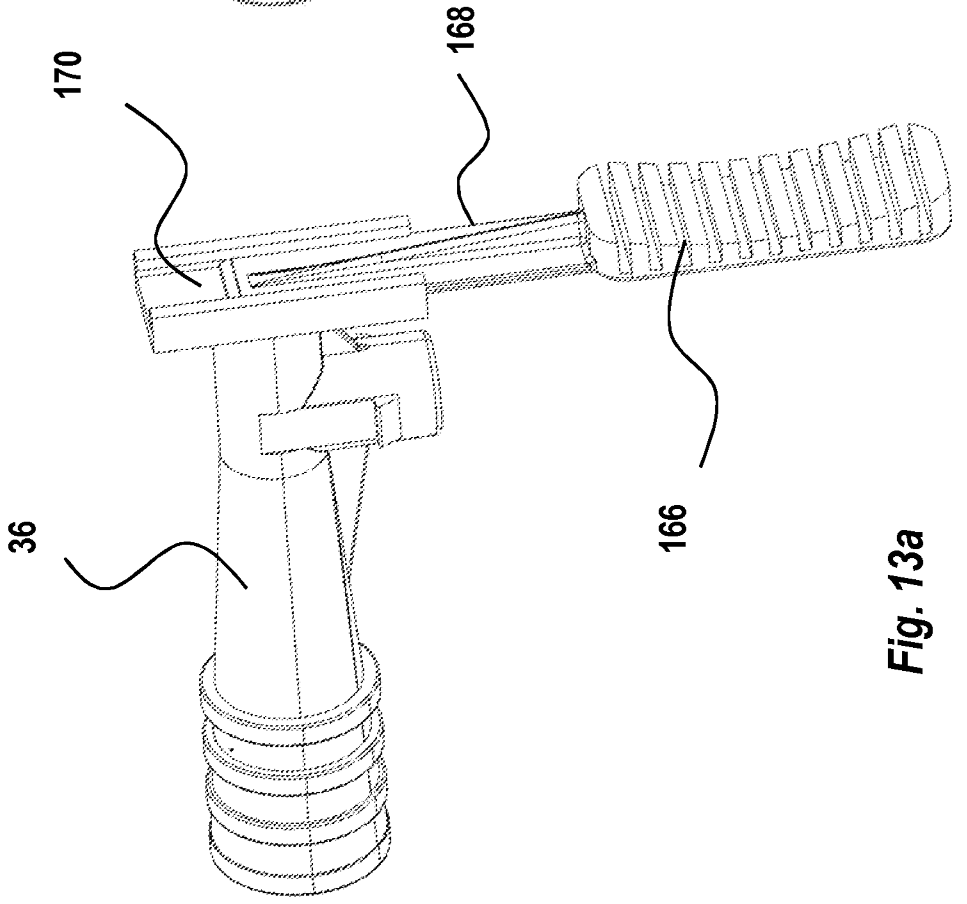
Figure 14:
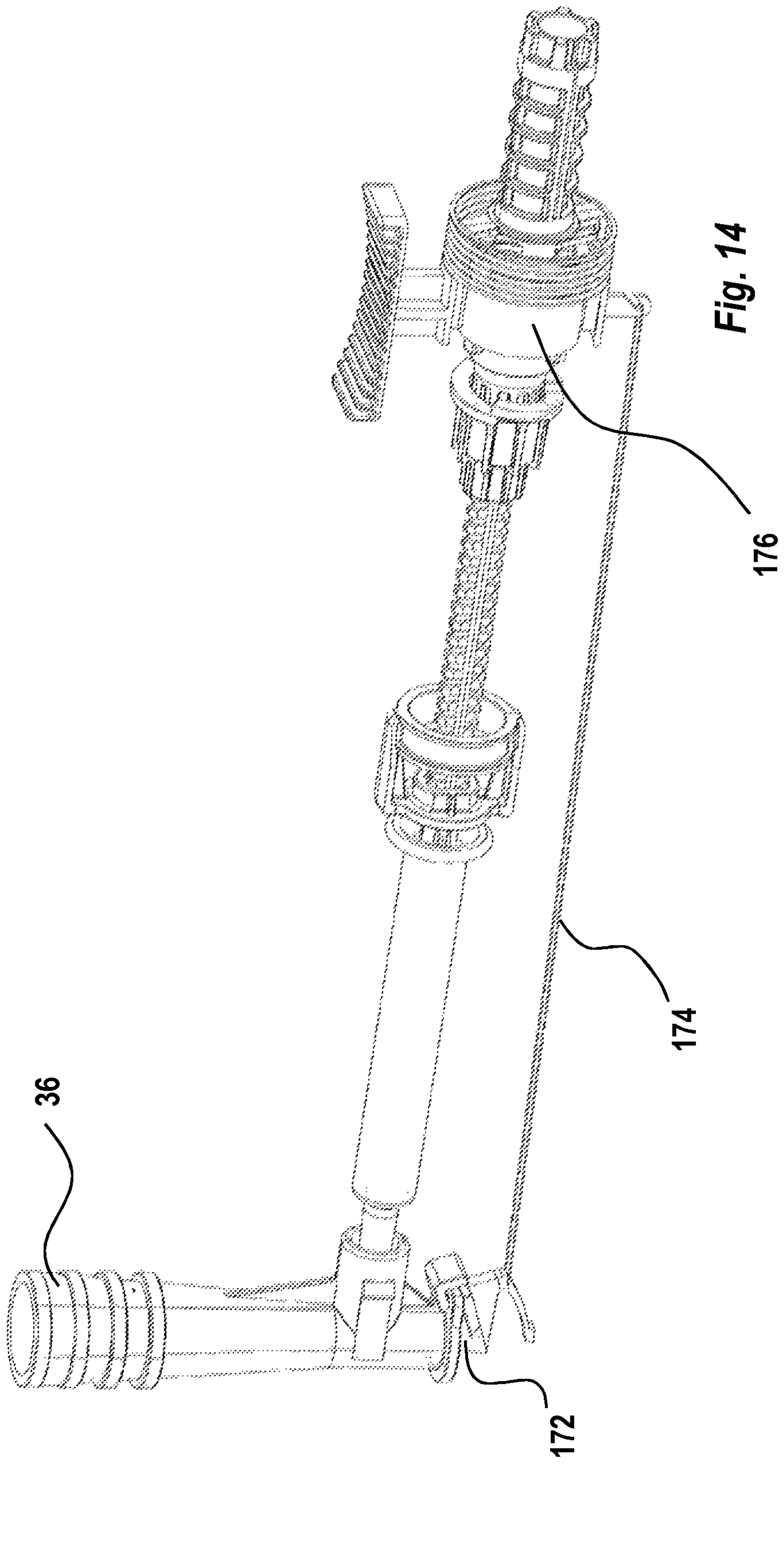
FIG. 14 is a detailed view of a third handling coordination mechanism, FIGS. 15*a, b* is a detailed view of a second handling coordination mechanism.

FIGS. 13*a, b* show a simple design having a sliding button 124 connected to the activation means of the device. The button is further provided with the blockage member as e.g. a tongue 168 arranged slidable in a seat 170 of the mouth piece, where the air opening of the mouth piece 36 is positioned. When the button 124 is not operated, the tongue 168 is blocking the air opening, preventing inhalation through the mouth piece 36, FIG. 13*a*. When the user then operates the button 166, the air opening is opened at the same time as the medicament is released in the mouth piece, FIG. 13*b*, thereby providing a coordination between inhalation and dose delivery.

Figure 15B:
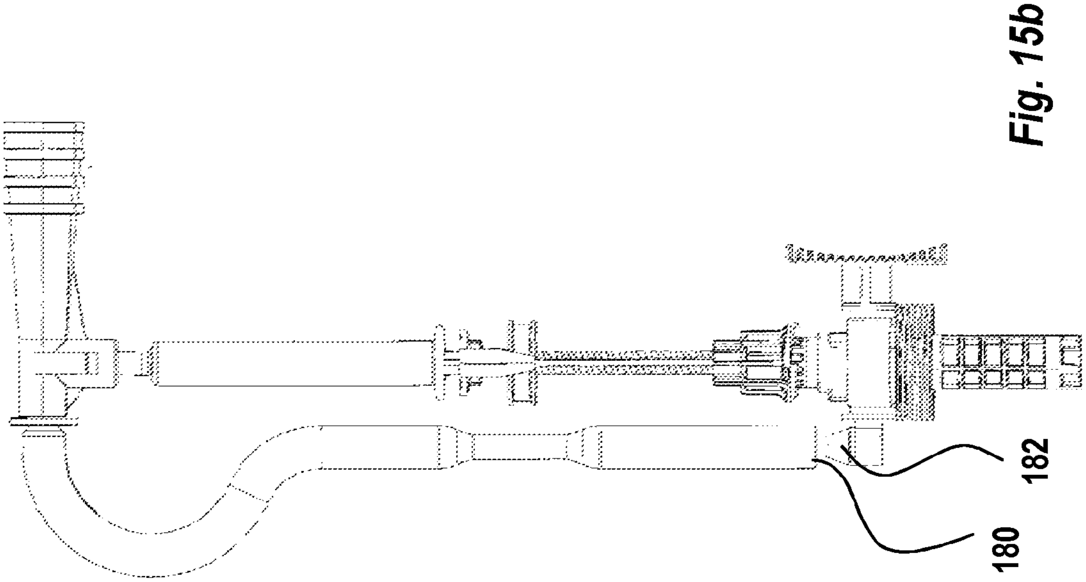
Figure 15A:
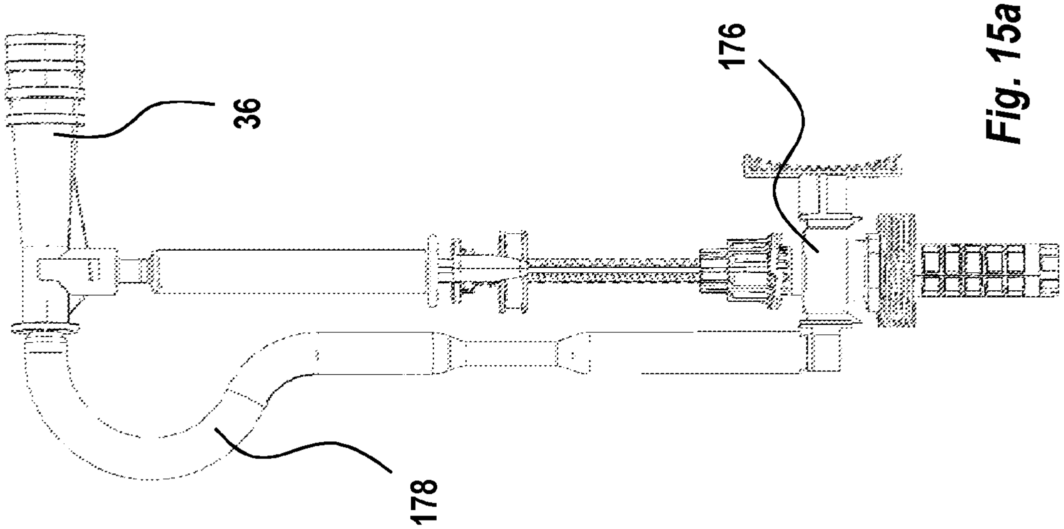

FIGS. 15*a* and 15*b* show a further variant having a tubular extension 178 of the mouth piece 36, where an opening 180 of the extension is adjacent an activation means 176. The tubular extension 178 may be provided with a restriction passage 184 for restricting the inhalation airflow and thereby improving pulmonary deposition. The blockage member as e.g. a plug or sealing member 182 is connected to the activation means 176 and movable from a position where it seals the opening 180, FIG. 15*a*, when the activation means is not operated, to an open position, FIG. 15*b*, when the activation means is operated and thereby enabling inhalation through the mouth piece. It is also conceivable that the sealing member 182 and the opening 180 are adapted with restriction means for the same purpose as mentioned above FIG. 14 shows a similar solution where the blockage member as e.g. a lid 172 is hingedly attached to the mouth piece between a closed position blocking the air opening of the mouth piece 36 to an open position where inhalation is enabled. As seen in figure the lid may be connected by a wire 174 or the like to activation means 176 such that the lid is moved and the passage is opened when the activation means 176 is operated.

Figure 16:
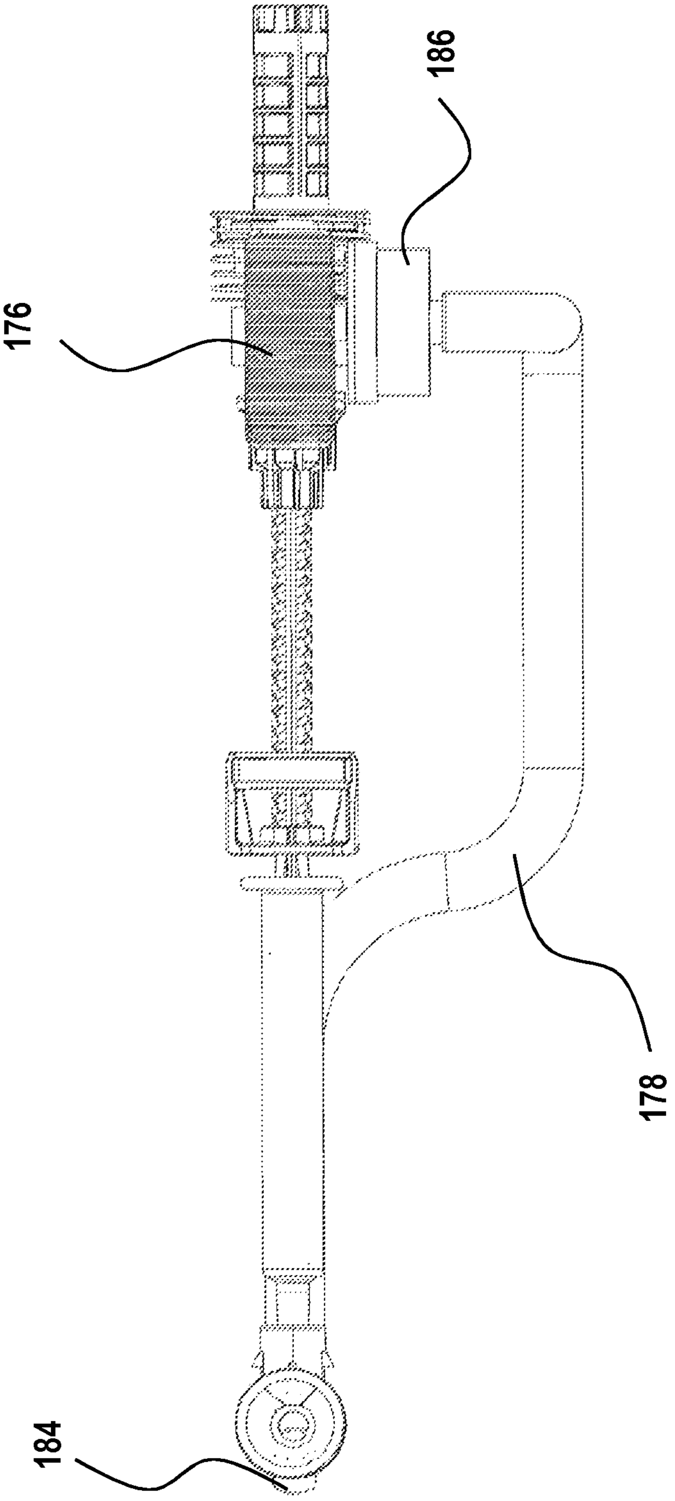
FIG. 16 is a detailed view of a fourth handling coordination mechanism, and FIGS. 17*a, b* is a detailed view of components comprised in the fourth handling coordination mechanism.
Figure 17B:
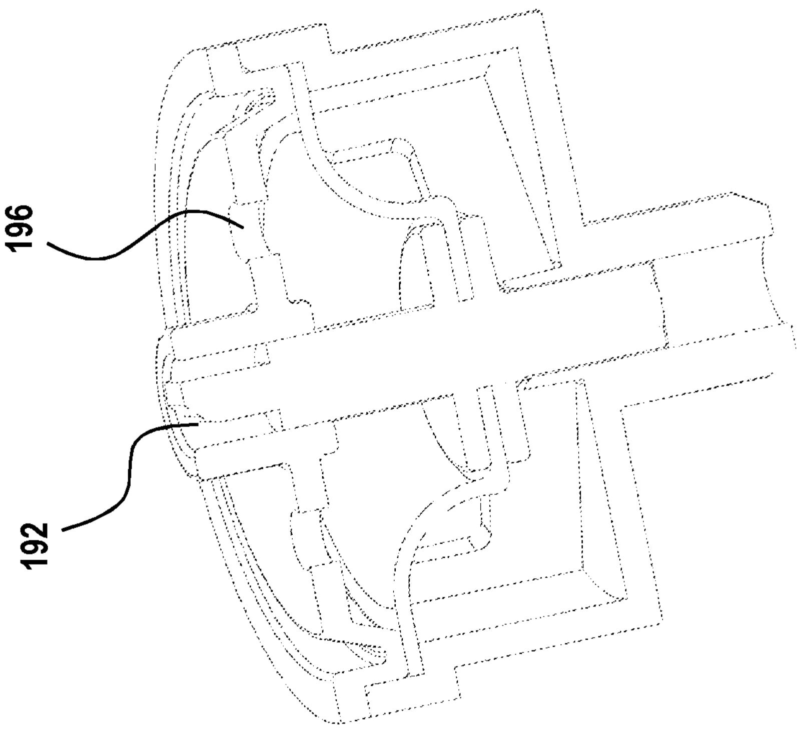
Figure 17A:
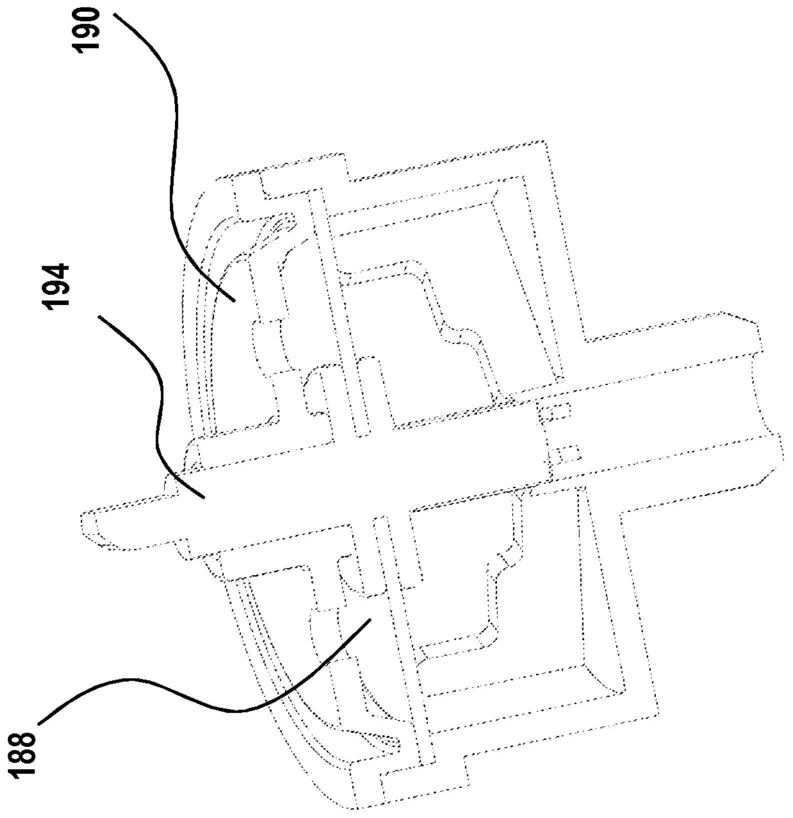

FIGS. 16 and 17 shows the variant where said handling coordination mechanism comprises an activation blockage mechanism operatively connected to said mouth piece such that said activation blockage mechanism is removed from said activation mechanism during inhalation through said mouth piece. This variant comprises a tubular extension 178 provided with an air inlet. The distal end of the extension 178 is here connected to a chamber 186, which chamber 186 is positioned adjacent the activation means 176. Inside the chamber 186 a silicone membrane 188, FIG. 17*a*, is positioned, dividing the chamber. The chamber is closed by a lid having a central passage through which a rod 194 extends and is movable. The rod 194 is attached to the membrane 188. The lid is further arranged with a number of air passages. This variant is intended to function such that when the device is not operated, i.e. there is no inhalation, the membrane 188 is unaffected and the rod 194 protrudes out of the passage, FIG. 17*a*, such that it blocks the movement of the activation means. When a user starts the inhalation, a pressure difference is created in the chamber 186 on both sides of the membrane 188 such that the rod is drawn into the chamber 186 due to the flexing of the membrane 188, FIG. 17*b*. The movement of the rod 194 frees the activation means and enables operation such that a dose of medicament is delivered.

It is apparent from the above description that there is immediate applicability of the device to medicament designed for the respiratory or pulmonary system, such as of course asthma. Other types of medicament and compositions could be used for treating cystic fibrosis and or its complications as well as chronic obstructive pulmonary disease.

It is to be understood that the embodiment described above and shown in the drawings is to be regarded only as a non-limiting example of the invention band that it may be modified in many ways within the scope of the patent claims.

The invention claimed is:

1. A metered liquid droplet inhaling device for delivering medicament, comprising:

a generally elongated tubular chassis having opposite distal and proximal ends;

a medicament container holder releasably connected to the chassis by a first engagement device;

a medicament container arranged inside the medicament container holder, wherein the container comprises a tubular form having at least one chamber configured for containing a composition, a proximal opening for allowing the composition to be expelled therefrom, and at least one axially movable piston having a rigid core, the at least one axially movable piston being coaxially movable along a long axis of the generally elongated tubular chassis;

a dose knob accessible outside the distal end of the chassis for setting a dose to be expelled by accumulating a rotational force;

a power supply mechanism configured for converting the rotational force into an axial force to be applied to the piston and thereby to create a pressure inside the medicament container;

an activation device in mechanical connection to the power supply mechanism;

a mouth piece mechanically connected to the proximal part of the container holder, wherein the mouth piece comprises a mouth engaging area and an air opening;

a droplet generator having a plurality of through passing orifices and arranged in the mouth piece, wherein the orifices are in fluid communication with the proximal opening of the container and with the mouth piece; and a rotating damping member mechanically connected to the power supply mechanism for damping an initial pressure peak inside the medicament container, the rotating damping member comprising a distal part protruding into a compartment in the dose knob that is filled with a viscous material, wherein the distal part rotates about an axis that is coaxial with the long axis of the generally elongated tubular chassis, and the distal part being separated from the piston on the long axis;

wherein at least the power supply mechanism and rotating damping member cooperate to generate the pressure inside the medicament container that is substantially constant during medicament delivery.

2. The device of claim 1, wherein the proximal end of the mouth engaging area comprises at least one guide device that is sensed by lips of a user for ensuring efficient airflow and for positioning the mouth piece at a predetermined distance from a pharynx of a user.

3. The device of claim 1, wherein a central axis of the mouth piece is in a range of 100-120° in relation to a central axis of the medicament container.

4. The device of claim 1, wherein the medicament container is a medicament cartridge or syringe.

5. The device of claim 1, wherein the medicament container is a dual-chamber cartridge or syringe having two separate components which are introduced to one another by mixing manually or automatically.

6. The device of claim 1, wherein the rotating damping member is mechanically connected to the power supply mechanism by at least one spline on the proximal part of the rotating damping member that cooperates with at least one spline groove in the power supply mechanism.

7. A metered liquid droplet inhaling device for delivering medicament, comprising:

a generally elongated tubular chassis having opposite distal and proximal ends;

a medicament container holder releasably connected to the chassis by a first engagement device;

a medicament container arranged inside the medicament container holder, wherein the container comprises a tubular form having at least one chamber configured for containing a composition, a proximal opening for allowing the composition to be expelled therefrom, and at least one axially movable piston, the at least one axially movable piston being coaxially movable along a long axis of the generally elongated tubular chassis;

a dose knob accessible outside the distal end of the chassis for setting a dose to be expelled by accumulating a rotational force;

a power supply mechanism configured for converting the rotational force into an axial force to be applied to the piston and thereby to create a pressure inside the medicament container;

an activation device in mechanical connection to the power supply mechanism;

a mouth piece mechanically connected to the proximal part of the container holder, wherein the mouth piece comprises a mouth engaging area and an air opening;

a droplet generator having a plurality of through passing orifices and arranged in the mouth piece, wherein the orifices are in fluid communication with the proximal opening of the container and with the mouth piece; and a rotating damping member mechanically connected to the power supply mechanism for damping an initial pressure peak inside the medicament container and having a distal part that rotates about an axis that is coaxial with long axis of the generally elongated tubular chassis, and the distal part being separated from the piston on the long axis;

wherein the power supply mechanism comprises:

a threaded plunger rod having opposite distal and proximal ends, and having its proximal end in contact with the piston of the medicament container;

a drive nut threadedly connected to the threaded plunger rod;

an arbor rotatably connected to the dose knob accessible outside the distal end of the chassis, the arbor being connected to the drive nut via an arbor extension and having a rotation axis that is substantially collinear with the long axis, wherein the arbor extension and the arbor are interconnected by a second engagement device that rotationally locks the arbor extension in an opposite direction when the arbor is rotated by the dose knob, wherein the arbor extension and the drive nut are interconnected by a third engagement device that rotationally locks but allows longitudinal movement of the drive nut in relation to the arbor extension;

a spring force mechanism having a first end connected to the arbor and a second end connected to a fixed point on the chassis such that the spring force mechanism is tensioned when the dose knob and the arbor are rotated; and a guide part arranged with guide ledges which cooperate with longitudinal grooves of the plunger rod that rotationally locks but allows longitudinal movement of the plunger rod in relation to the guide part; and at least the power supply mechanism and rotating damping member cooperate to generate the pressure inside the medicament container that is substantially constant during medicament delivery; and rotation of the arbor rotates the rotating damping member.

8. The device of claim 7, wherein the activation device is releasably interconnected to the arbor extension by a fourth engagement device that rotationally locks the arbor extension in one direction when the arbor is rotated and the spring force mechanism is tensioned, and that allows rotation when the fourth engagement device is moved apart, such that the arbor, the arbor extension, and the drive nut are rotated in the opposite direction forcing the plunger rod to move axially, thereby exerting pressure on the piston for expelling a predetermined quantity of the medicament through the medicament droplet generator and the mouth piece.

9. The device of claim 8, further comprising a pressure release mechanism comprising slanting wedge-shaped surfaces arranged on the drive nut and slanting wedge-shaped surfaces arranged on a fixed inner annular surface of the chassis, which slanting wedge-shaped surfaces abut each other such that they move out of contact near an end of delivery of the predetermined quantity when the drive nut is rotated for reducing the pressure inside the medicament container at end of delivery.

10. The device of claim 9, wherein the spring force mechanism is a spiral strip drive spring.

11. The device of claim 7, wherein the dose knob and the arbor are releasably connected to each other by a sixth engagement device during dose setting and tensioning of the spring force mechanism, and the dose knob is rotationally locked by a fifth engagement device when the dose knob and the arbor are disconnected from each other.

12. The device of claim 11, wherein the rotating damping member is arranged between the arbor and the dose knob and is configured for damping initial movement of the arbor during delivery of a dose and thereby an initial pressure peak inside the medicament container.

13. The device of claim 12, wherein the-rotating damping member comprises a proximal part rotationally connected to the arbor and the distal part protrudes into a compartment in the dose knob, and the compartment is filled with a viscous material.

14. The device of claim 13, wherein the rotating damping member is mechanically connected to the power supply mechanism by at least one spline on the proximal part of the rotating damping member that cooperates with at least one spline groove in a central passage of the arbor.

15. The device of claim 7, wherein the chassis and the medicament container holder are releasably connected to each other by an engagement device.

16. The device of claim 7, wherein the piston has a rigid core.

17. A metered liquid droplet inhaling device for delivering medicament, comprising:

a generally elongated tubular chassis having opposite distal and proximal ends;

a medicament container holder releasably connected to the chassis by a first engagement device;

a medicament container arranged inside the medicament container holder, wherein the container comprises a tubular form having at least one chamber configured for containing a composition, a proximal opening for allowing the composition to be expelled therefrom, and at least one axially movable piston that is coaxially movable along a long axis of the generally elongated tubular chassis;

a dose knob accessible outside the distal end of the chassis for setting a dose to be expelled by accumulating a rotational force;

a power supply mechanism configured for converting the rotational force into an axial force to be applied to the piston and thereby to create a pressure inside the medicament container;

an activation device in mechanical connection to the power supply mechanism;

a mouth piece mechanically connected to the proximal part of the container holder, wherein the mouth piece comprises a mouth engaging area and an air opening;

a droplet generator having a plurality of through passing orifices and arranged in the mouth piece, wherein the orifices are in fluid communication with the proximal opening of the container and with the mouth piece;

a rotating damping member mechanically connected to the power supply mechanism for damping an initial pressure peak inside the medicament container, wherein the rotating damping member comprises a distal part protruding into a compartment in the dose knob that is filled with a viscous material, wherein the distal part rotates about an axis that is coaxial with the long axis of the elongated tubular chassis, and the distal part being separated from the piston on the long axis; and a handling coordination mechanism configured for coordinating inhalation and delivery of medicament;

wherein at least the power supply mechanism and rotating damping member cooperate to generate the pressure inside the medicament container that is substantially constant during medicament delivery.

18. The device of claim 17, wherein the handling coordination mechanism comprises a blockage member positioned in the mouth piece, and the blockage member is operatively connected to the activation device such that the blockage member is removed from the mouth piece when the activation device is operated.

19. The device of claim 18, wherein the handling coordination mechanism comprises an activation blockage mechanism operatively connected to the mouth piece such that the activation blockage mechanism is removed from the activation device during inhalation through the mouth piece.

20. The device of claim 17, wherein the piston has a rigid core.

* * * * *